US012617517B2

(12) United States Patent
Slavin et al.

(10) Patent No.: US 12,617,517 B2
(45) Date of Patent: May 5, 2026

(54) SYSTEM AND METHOD FOR FUMIGATING A VESSEL WITH CREW PROTECTION

(71) Applicant: FINTRAN AUSTRALIA PTY LTD, Victoria (AU)

(72) Inventors: Matthew Brian Slavin, Victoria (AU); Aric Jana, Victoria (AU)

(73) Assignee: FINTRAN AUSTRALIA PTY LTD, Victoria (AU)

( * ) Notice: Subject to any disclaimer, the term of this patent is extended or adjusted under 35 U.S.C. 154(b) by 713 days.

(21) Appl. No.: 17/928,115

(22) PCT Filed: May 26, 2021

(86) PCT No.: PCT/AU2021/050505
§ 371 (c)(1),
(2) Date: Nov. 28, 2022

(87) PCT Pub. No.: WO2021/237290
PCT Pub. Date: Dec. 2, 2021

(65) Prior Publication Data
US 2023/0219663 A1     Jul. 13, 2023

(30) Foreign Application Priority Data

May 26, 2020    (AU) ................................ 2020901707
May 26, 2020    (AU) ................................ 2020901708

(51) Int. Cl.
*B63J 2/08*        (2006.01)
*A01M 13/00*       (2006.01)
(Continued)

(52) U.S. Cl.
CPC . *B63J 2/08* (2013.01); *A61L 2/20* (2013.01); *A61L 2/24* (2013.01); *A61L 2/26* (2013.01);
(Continued)

(58) Field of Classification Search
CPC ..... A61L 2/20; A61L 2/24; A61L 2/26; A61L 9/122; B63J 2/08
See application file for complete search history.

(56) References Cited

U.S. PATENT DOCUMENTS 2,120,563 A     6/1938  Lamb
2,160,831 A     6/1939  Colby et al.
(Continued)

FOREIGN PATENT DOCUMENTS

CN     206125390 U     4/2017
CN     207284926 U     5/2018
(Continued)

OTHER PUBLICATIONS

International Search Report and Written Opinion for International Patent Application No. PCT/AU2021/050505 mailed on Aug. 9, 2021.
(Continued)

*Primary Examiner* — Sean E Conley
(74) *Attorney, Agent, or Firm* — Christopher R. Christenson; Kelly, Holt & Christenson PLLC

(57) ABSTRACT

A methods and systems of fumigating a vessel include delivering fumigant to a cargo area of the vessel. In particular, the vessel may be a roll-on/roll-off vessel. In such a system, an air pressure system is provided for maintaining a selected minimum pressure differential between a selected area of the vessel above the cargo area and the cargo area, such that pressure of the selected area is greater than the cargo area. A control system may maintain the pressure differential.

17 Claims, 19 Drawing Sheets

(51) Int. Cl.

| | |
|---|---|
| *A61L 2/20* | (2006.01) |
| *A61L 2/24* | (2006.01) |
| *A61L 2/26* | (2006.01) |
| *A61L 9/12* | (2006.01) |
| *B63B 25/00* | (2006.01) |
| *B63B 57/04* | (2006.01) |

(52) U.S. Cl.
CPC ............ *A61L 9/122* (2013.01); *B63B 25/008* (2013.01); *B63B 57/04* (2013.01); *A01M 13/00* (2013.01); *A61L 2202/14* (2013.01); *A61L 2202/15* (2013.01)

(56) References Cited

U.S. PATENT DOCUMENTS

| | | | |
|---|---|---|---|
| 2,599,925 | A | 6/1952 | Lamb |
| 3,097,916 | A | 7/1963 | Carl et al. |
| 4,515,070 | A | 5/1985 | Bobjer et al. |
| 5,655,963 | A | 8/1997 | Paschke et al. |
| 6,402,613 | B1 | 6/2002 | Teagle |
| 7,222,888 | B1 | 5/2007 | Piety et al. |
| 10,349,648 | B2 | 7/2019 | Atanackovic et al. |
| 2005/0074359 | A1 | 4/2005 | Krieger et al. |
| 2016/0113265 | A1 | 4/2016 | Sorrondeguy et al. |

FOREIGN PATENT DOCUMENTS

| | | | |
|---|---|---|---|
| DE | 913879 | C | 6/1954 |
| EP | 2605956 | B1 | 1/2019 |
| GB | 2250200 | A | 6/1992 |
| JP | S57147200 | A | 9/1982 |
| JP | S57147200 | U | 9/1982 |
| JP | S6029399 | A | 2/1985 |
| JP | 2020022415 | A | 2/2020 |
| KR | 20130010389 | A | 1/2013 |
| KR | 101291140 | B1 | 8/2013 |
| KR | 20170061997 | A | 6/2017 |
| SU | 185626 | A1 | 8/1966 |
| WO | 2018150904 | A1 | 8/2018 |

OTHER PUBLICATIONS

Australian International Search Report mailed on Jan. 11, 2021 for Australian Patent Application No. 2020901708.

International Search Report mailed on Aug. 4, 2021 for International Patent Application No. PCT/AU2021/050504.

International Search Report mailed on Aug. 9, 2021 for International Patent Application No. PCT/AU2021/050505.

African Regional Intellectual Property Organization, Search Report mailed on Jul. 15, 2024 for African Patent Application No. AP/P/2022/014586, 1 page.

European Patent Office, Extended European Search Report mailed Jun. 27, 2024 for EP Application No. 21811844.6, 23 pages.

European Patent Office, Extended European Search Report mailed May 23, 2024 for EP Application No. 21813072.2, 11 pages.

SYSTEM AND METHOD FOR FUMIGATING A VESSEL WITH CREW PROTECTION

CROSS REFERENCE TO RELATED APPLICATION(S)

This application relates to, and claims the benefit and priority from International Patent Application No. PCT/AU2021/050505 filed on May 26, 2021 that published as International Patent Publication No. WO 2021/237290 on Dec. 2, 2021, which claims the benefit and priority from Australian Patent Application No. 2020901707 and Australian Patent Application No. 2020901708, both filed on May 26, 2020, the entire disclosures of which are incorporated herein by reference.

FIELD OF THE INVENTION

The present invention relates to a system and method for fumigating a vessel. The invention has particular application to fumigation of roll-on/roll-off vessels. The present invention is also directed to a method of fumigating a roll-on/roll-off vessel. Furthermore, the invention relates to a temporary bulkhead. Although the present invention is directed to roll-on/roll-off vessels, certain aspects of the invention are by no means limited to these types of vessels and may have broader application to cargo vessels and other types of sea-faring vessels.

The reader is also directed to our other coexisting application filed coincidentally: "System and method for fumigating a vessel with exhaust" concerning aspects of the present invention described herein but not claimed. The entire contents of that coexisting application are incorporated herein by reference.

BACKGROUND

It is a requirement in many jurisdictions that cargo onboard a cargo-carrying vessel be fumigated prior to unloading. Fumigation of an infested vessel may also be necessary. The fumigation process involves releasing fumigant into a cargo area of the vessel to eliminate, reduce, or avoid infestation of the cargo by insects or other undesirable pests. The fumigant may be provided in solid form and located in the cargo area, or may be provided in gaseous form and piped into the cargo area. The fumigation gases are usually toxic to human beings.

The fumigation process may be conducted en-route, when anchored, or when moored at quay, and is typically conducted by specially trained personnel with specialised equipment. In most instances, members of the crew of the vessel will be located on the vessel during the fumigation process, and thus it is imperative that the fumigation process is conducted in such a manner that ensures that the crew (and the specially trained fumigation personnel) are not exposed to the toxic fumigant. Access to parts of the vessel such as the engine room and mooring lines may also be required during fumigation.

A bulk carrier is a vessel specifically designed to transport unpackaged bulk cargo, such as grains, coal, ore, and other similar loose cargo. Bulk carriers typically comprise one or more separate cargo holds arranged fore to aft in the vessel. Grain or other unpackaged bulk goods may be loaded into and unloaded from the cargo holds by, for example, one or more cranes located on the deck of the vessel. Alternatively, conveyor loaders, shoreside cranes, or pneumatic loaders may be used to load and unload cargo. Each of the cargo holds typically also includes a hatch for closing the opening to the cargo holds.

In bulk carriers, the accommodation area of the vessel and the engine room of the vessel are typically located aft of the cargo holds, with the accommodation area provided above the engine room. The cargo holds are separated from the engine room by a vertically extending bulkhead. The accommodation area is physically separated from the cargo holds, by being physically removed from the cargo holds by the intervening engine room and furthermore by two physical barriers including the vertically extending bulkhead and the deck between the engine room and the accommodation area. Due to this physical separation, it has generally been relatively safe to fumigate each of the cargo holds of a bulk carrier, subject to inspection of the vessel.

A new challenge presents itself in safely fumigating roll-on/roll-off vessels, also known as RORO vessels. In vessels of this sort, the cargo area typically extends substantially the entire length of the vessel, and is arranged in decks within the vessel.

The decks are interconnected by upright passageways such as staircases and ladders and the decks are joined by ramps. Further, the decks are grouped into watertight or gas tight zones, with typically 2 decks in each zone, although some vessels may include more than 2 decks per zone. Normally, RORO vessels are arranged into approximately 4 zones and each zone is independently ventilated. The cargo area is configured in this way so that breakbulk cargo such as wheeled cargo can be rolled onto or driven into the cargo area.

In a RORO vessel, the accommodation area is typically located upon the weather deck of the vessel, with only plate steel and a floor covering separating the accommodation area from the uppermost deck of the cargo area. Thus, any openings or small cracks within this plate steel structure could result in fumigant entering the accommodation area from the uppermost deck of the cargo area. Openings or small cracks are prevalent in seagoing vessels due to the stresses placed on the vessel during seafaring.

The arrangement of the accommodation area in a RORO vessel presents another challenge for exhausting the fumigant from the cargo area. Ventilation systems which service the cargo decks have been specifically designed to ventilate fuel vapour from the cargo area. Each zone (watertight or gas tight group of cargo decks) of the vessel is serviced by its own group of mechanical ventilators (supply and exhaust, as discussed below), wherein the ventilators may be controlled as a group or each ventilator in the group may be individually controlled independent of any other ventilators in that group. In general, the systems have been designed to typically achieve 20-30 air changes in each zone during loading/unloading operations and 10 air changes per hour during navigation.

RORO vessels typically have one of two types of ventilation systems for the cargo area:

1. Supply and Exhaust Mechanical Ventilators:

Supply and Exhaust ventilators are arranged around the perimeter of the weather deck. Some vessels may have as many as 70 or more mechanical ventilators. Mechanical Ventilators serve as either supply, exhaust, or reversable supply mechanical ventilators. Each zone of the vessel is ventilated by a group of supply and exhaust mechanical ventilators which work together to exchange air in the zone. Each zone has multiple ducts connected to the group of mechanical ventilators through which the air is exchanged (supply and exhaust ducts).

Supply Mechanical Ventilators supply air from the weather deck into the zone.

Exhaust Mechanical Ventilators exhaust air from the zone into the atmosphere on the weather deck.

The ventilators may be dedicated supply ventilators and dedicated exhaust ventilators, as the case may be. Some fans can be run alternatively in supply and exhaust mode and the mode is controlled by the operator. Such ventilators are referred to as reversible supply ventilators. Depending on how many air changes need to be achieved during navigation or loading/unloading, some mechanical ventilators may be used/not used.

The mechanical ventilators are typically located very close to the accommodation area and the engine room supply ventilation intake, sometimes barely a few metres. Type 1 is prevalent with new RORO vessels.

2. Supply Mechanical Ventilators and Vent Houses:

Supply mechanical ventilators are located around the forward and midship perimeter of the ship.

Ductwork connected to these supply mechanical ventilators supplies fresh air into the cargo area.

Vent houses are located at the aft end of the vessel (also on the portside and starboard perimeter). Each zone has its own dedicated vent houses.

Ductwork connects each zone to the vent houses.

Fresh air is forced into each zone by the supply mechanical ventilators and the atmosphere is exhausted out through the vent houses.

In either case, the mechanical ventilators/vent houses are close to the engine room air intake and the air-conditioning intake for the crew accommodation. Thus, the relative proximity presents a risk to the crew if the mechanical ventilators/vent houses vent fumigant during fumigation.

In addition, the mechanical ventilators are designed with mechanically operated vents which open and close but which are directed downwardly in either case to avoid entry of rain. Therefore, the mechanical ventilators blow down onto the weather deck. Venting the fumigant from the cargo area through the mechanical ventilators creates a likelihood of fumigant stratifying and remaining on the weather deck. This poses a risk to crew requiring access to the engine room, moorings or in the case of evacuation.

Another special feature of RORO vessels as distinguished from bulk carriers is that RORO vessels sit proud of the water compared to bulk carriers due to the lower density of the cargo in RORO vessels. Thus, mooring lines will be lower down, typically on decks 4 or 5 and thus require stairwell access so that the crew can adjust the mooring lines to take account of tidal movement. In contrast, the mooring lines for a bulk carrier are arranged on the weather deck.

Other areas of the vessel may require access during fumigation. For example, the engine room, which is is sandwiched between cargo zones, may require access during fumigation. For example, auxiliary generators typically run during fumigation. Should an alarm condition arise, the crew will then require access to the engine room. Fumigant entering the engine room or access ways will be harmful to the health of the crew.

It is an object of the present invention to provide a system/method for fumigating a RORO vessel. It is also an object of the present invention to provide a temporary bulkhead configured to fluidly seal an entryway of a vessel. Another object of the present invention is to at least provide the public with a useful choice over known systems, methods and equipment.

As used herein, the term "roll-on/roll-off vessel" or "RORO vessel" refers to any vessel in which wheeled or tracked cargo is rolled onto or driven into the cargo decks of the vessel, typically via a stern ramp or a side ramp. Examples of such vessels include a pure car and truck carrier (PCTC), a large car and truck carrier (LCTC), and a pure car carrier (PCC).

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY

1. System for Fumigating a Vessel

In a first aspect, there is provided, a system for fumigating a vessel, wherein the system is ancillary to the vessel, the system comprising:

a fumigant delivery system for delivering fumigant to a cargo area of the vessel; and an air pressure system for maintaining a selected minimum pressure differential between a selected area of the vessel above the cargo area and the cargo area, such that pressure of the selected area is greater than the cargo area.

In an embodiment, the vessel is a roll-on/roll-off (RORO) vessel. Preferably, the air pressure system includes a controller to maintain the pressure differential throughout fumigation and exhaust.

The system is preferably ancillary in that it is not in the body of the vessel, nor part of the machinery, tackle, gear and other accessories of the vessel. The control system is also preferably ancillary equipment brought into fumigate a vessel. As described, many of the aspects are used quayside. Components of the air pressure system are preferably portable. For example, the air pressure system may include one or more controllers, one or more fans, one or more variable speed drives, and related sensors, some or all of which may be portable.

Preferably, the selected area comprises the accommodation area of the vessel. However, the selected area may alternatively or additionally include other areas intended for human occupancy such as the engine room, access corridors and stairwells to the engine room or mooring lines.

The fumigant may be a pesticide. Alternatively, the fumigant may comprise an insecticide, disinfectant, purifier, bactericide, decontaminant, antiseptic, sanitiser, vaccine, anti-viral, or vapour.

Preferably, the fumigant delivery system includes one or more first conduits for delivering fumigant in a gaseous form, wherein a first end of the one or more first conduits is connected to a source of fumigant, and a second end of the one or more first conduits is connected to the cargo area of the vessel for delivering the gaseous fumigant thereto.

Preferably, the air pressure system includes one or more second conduits for delivering air, wherein a first end of the one or more second conduits is connected to a source of air, and a second end of the one or more second conduits is connected to the selected area of the vessel. As described above, the selected area is preferably the accommodation area of the vessel.

Preferably, the one or more second conduits are configured to deliver the air to the accommodation area such that a pressure differential between the accommodation area and the cargo area is substantially maintained. The pressure differential is preferably at least 50 Pa, and more preferably is between 50 Pa and 100 Pa. The pressure differential may be a predetermined or preselected pressure differential or alternatively determined according to measure parameters or the operational guidelines. The pressure differential may be constant. Alternatively, the pressure differential may vary throughout the course of the fumigation, provided a minimum pressure differential is maintained. The pressure differential may vary according to other measured parameters. The selected minimum pressure differential may be maintained throughout fumigation and preferably extended beyond fumigation, at least until clearance of the fumigant from the cargo area.

In an embodiment, the air pressure system may maintain the pressure differential by maintaining a relatively high pressure within the accommodation area, thereby ensuring that a pressure differential will exist between the accommodation area and the cargo area (the cargo area being typically at atmospheric pressure).

The air pressure system and/or the fumigant delivery system are preferably controlled by a controller or respective controllers. The controller preferably forms part of a control system. The or each controller is pre-configured either at manufacture or at routine servicing or calibration. Calibration includes re-calibration.

The one or more first conduits of the fumigant delivery system are preferably sealingly connected at their second ends to a first bulkhead located at an entry to the cargo area. The first bulkhead is preferably configured to fluidly receive and deliver the gaseous fumigant to the cargo area. In one embodiment, the first bulkhead includes one or more openings therein configured to be respectively connected to the one or more first conduits to thereby deliver the gaseous fumigant to the cargo area. The one or more openings may include a respective one or more valves. The one or more valves may be one-way valves. The one or more openings may also be used to transfer gas samples from the cargo area across the first bulkhead in order to analyse the gas samples outside of the cargo area. Preferably, the first bulkhead includes a seal configured to fluidly seal the entry to the cargo area. The seal is preferably in the form of a rubber extrusion. The seal is preferably located on the bulkhead according to the form and type of the entryway to be sealed. The first bulkhead may include one or more other openings configured to deliver power and/or data across the first bulkhead. The first bulkhead may be fitted to the watertight steel doorway. This type of door nearly always has a protruding steel flange that runs around the perimeter of the doorway. Normally the protruding steel flange jambs into the rubber packing on the door to create a seal. There are two preferred options to create a seal using temporary bulkhead:

1) Fit a rubber extrusion to the protruding steel flange that runs around permitter of the doorway. The rubber extrusion creates a seal with the flat surface on the bulkhead; or 2) Apply a flat rubber or foam (butyl tape) flat extrusion to the bulkhead using an adhesive. The protruding steel flange that runs around the doorway then jambs into the rubber surface on the backside of the bulkhead.

The system preferably further comprises one or more other temporary bulkheads where access ways need to be sealed but pass through services (conduit or power cables etc.). The one or more other bulkheads may be similar to the first bulkhead. For instance, there are lots of entry points into each cargo zone. Each escape trunk (vertical access way located around the perimeter of the vessel) will have a watertight door or hatch between cargo zones. Bulkheads are preferably fitted on those access ways (doors/hatches) that need to be fitted with services. Preferably, a bulkhead is located at at least one entry into each cargo zone of the vessel, and thus each cargo zone may be independently fumigated of any other cargo zone, if desired. For example, the first bulkhead may be located at the entry to the first cargo zone, and may be fluidly connected via a conduit to another bulkhead located at an entry to the second cargo zone, and thus fumigant may be delivered to the second cargo zone.

The system preferably further comprises a plurality of recirculation fans located within each cargo zone. The plurality of recirculation fans are configured to disperse the gaseous fumigant throughout the respective cargo zone. The one or more first conduits are preferably fluidly connected, via the first bulkhead (or via the respective bulkhead located at the entry to the respective cargo zone), to the plurality of recirculation fans to thus disperse the fumigant throughout the cargo zone. In a preferred embodiment, each deck within a cargo zone comprises two recirculation fans, wherein a first fan is located at midship on a starboard side of the vessel, and a second fan is located at midship on a port side of the vessel. The first fan and second fans preferably face in opposite directions within the vessel. For example, the first fan may face towards an aft end of the vessel, and the second fan may face towards a fore end of the vessel. The plurality of recirculation fans may be powered by power delivered through the one of more other openings in the first bulkhead (or the one or more openings in the one or more other bulkheads). The plurality of recirculation fans may be powered by a power source located onboard the vessel, or by a power source located remote of the vessel.

The one or more second conduits are preferably sealingly connected at their second ends to a second bulkhead located at an entry to the accommodation area. The second bulkhead is preferably configured to fluidly receive and deliver the air to the accommodation area. In one embodiment, the second bulkhead includes one or more openings therein configured to be respectively connected to the one or more second conduits to thereby deliver the air to the accommodation area. The one or more openings may include a respective one or more valves. The one or more valves may be one-way valves. Preferably, the second bulkhead includes a seal configured to fluidly seal the entry to the accommodation area. The second bulkhead may include one or more other openings configured to deliver power and/or data across the second bulkhead.

The gaseous fumigant may comprise any one or more of: sulfuryl fluoride, formaldehyde, methyl bromide, chloropicrin, iodoform, hydrogen cyanide, nitrogen, ethyl formate and ethanedinitrile. Fumigants may also be delivered with a carrier gas such as nitrogen or carbon dioxide.

The source of the fumigant may vary. In one embodiment, the fumigant may be provided by a mobile vehicle containing gaseous fumigant. The gaseous fumigant is typically stored in gas cylinders within the mobile vehicle. The gas cylinders may be arranged into separate groups. Each of gas cylinders in a group may be fluidly connected via a manifold. Two first conduits may extend from each manifold and deliver gaseous fumigant into a respective cargo zone. Each of the first conduits may have a diameter of between approximately ¼ inch (6.35 mm) to 1 inch (25.4 mm), but is preferably about ⅜ inch (9.53 mm).

In an alternative arrangement, the fumigant may be provided in a liquid form and vaporised quayside or on-board. Vaporisation methods include:

a) introduction of the liquid fumigant into a jetstream of the recirculation fans on each deck. This is appropriate for sulfuryl fluoride;

b) heat-exchanger vaporiser—such an arrangement could be provided on each cargo deck.

c) air-assisted atomisation whereby the liquid fumigant is pressurised before being introduced into the jetstream of the recirculation fans—such an arrangement could be provided on each cargo deck adjacent the recirculation fans d) fumigant liquid ethyl formate is dissolved in liquid CO2 and delivered from the quayside to the vessel as a mixture, with release resulting in heating by the atmosphere and vaporisation.

In a preferred embodiment, each of the one or more second conduits are connected at their first ends to a respective one or more fans. The one or more fans are configured to draw air into the respective one or more second conduits such that the air can be delivered by the one or more second conduits to the selected area of the vessel, such as the accommodation area. The one or more fans are preferably controlled by the controller via a variable speed drive (VSD). Preferably, the controller controls at least a speed of the one or more fans via the variable speed drive. In an embodiment, the VSD may be integrated with the controller. Alternatively, the VSD may be separate from the controller and operatively controlled by the controller.

In a preferred embodiment, the air pressure system comprises three second conduits configured to deliver the air to the selected area of the vessel, such as the accommodation area. In this embodiment, the air pressure system further comprises three fans, wherein each of the fans is connected to a respective first end of each of the three second conduits. The second conduits are preferably respective ducts each having a diameter of 450 mm.

Preferably, the source of air is environmental air located quayside of the vessel. Alternatively, the source of air may be drawn from below the weather deck of the vessel or on the weather deck at the forward end of the vessel. In this embodiment, one or more fans may be located on the weather deck of the vessel, and a respective one or more conduits may be connected to the one or more fans at a first end thereof. A second end of the one or more conduits may be passed over the side of the vessel so as to draw fresh air from below the weather deck.

Preferably, the source of air is located remote from the source of fumigant. Preferably, the source of air is located remote of the vessel.

The system preferably further comprises a low-range monitoring system comprising an air quality monitor located at or adjacent the source of air. Preferably, the air quality monitor is located substantially adjacent at least one of the first ends of the one or more second conduits. The air quality monitor may be configured to detect the presence of one or more of: gaseous fumigant, carbon dioxide, carbon monoxide, and other volatile organic compounds (VOCs). The low-range monitoring system may further comprise one or more other monitors or sensors located in other areas typically occupied by the crew of the vessel, such as the engine room for example. Each of the monitors or sensors of the low-range monitoring system can be configured to detect the presence of each of the abovementioned compounds. For gaseous fumigant comprising sulfuryl fluoride, each of the monitors or sensors of the low-range monitoring system are configured to detect sulfuryl fluoride in a range of concentrations from about 0.5 ppm to 230 ppm with a resolution of 0.1 ppm. However, different levels will apply for the various different fumigants. Each of the monitors or sensors of the low-range monitoring system preferably transmit their respective measurements to the controller.

The fumigant delivery system may further comprise a high-range monitoring system. The high-range monitoring system may comprise a plurality of monitors or sensors located in each of the cargo zones of the vessel. Each of the monitors or sensors of the high-range monitoring system can be configured to detect the presence of the gaseous fumigant in the cargo zones in order to determine the efficacy of the fumigation operation. For gaseous fumigant comprising sulfuryl fluoride, each of the monitors or sensors of the high-range monitoring system are configured to detect sulfuryl fluoride in a range of concentrations from about 5,000 ppm to 15,000 ppm in order to determine the efficacy of the fumigation operation. However, different levels will apply for the various different fumigants. Each of the monitors or sensors of the high-range monitoring system preferably transmit their respective measurements to the associated controller.

The controller(s) of the air pressure system and the low-range monitoring system may be integrated and operable to ensure the continued operation of the air pressure system to maintain the differential pressure while the low range monitoring system detects levels of gaseous fumigant in manned areas e.g. accommodation and/or at the intake to the pressure system. A safety feature may preclude discontinuance of the air pressure system if the low range monitoring system detects fumigant at the intake of the air pressure system. Another safety feature may lie in increasing the pressure within a manned area such as the accommodation system if the low range monitoring system detects fumigant within the manned area. For example, pressures up to 250 Pa (relative to the uppermost cargo hold or outside environment) may be tolerated in manned areas. In an alternative embodiment, the high-range monitoring system may comprise a single monitor or sensor. In this embodiment, one or more gas sampling lines may be located throughout the cargo area and connected at one end to a manifold. The manifold may be connected to the monitor or sensor, and a pump may be used in order to pump gas samples to the monitor or sensor via the one or more gas sampling lines. In this embodiment, the monitor or sensor may be located within the cargo area or outside of the cargo area. In either case, the monitor or sensor preferably transmits its measurements to the associated controller. If the monitor or sensor is located outside of the cargo area, the one or more gas sampling lines may be routed through any of the temporary bulkheads, as required.

The air pressure system preferably further comprises a first pressure sensor located in the cargo area, and a second pressure sensor located in the selected area, such as the accommodation area. In an embodiment in which the vessel is a RORO vessel, the cargo area may comprise a plurality of cargo zones arranged generally vertically within the vessel. In this embodiment, the accommodation area may be located at least partially above an uppermost one of the plurality of cargo zones. In a preferred embodiment, the first pressure sensor is located in the uppermost one of the plurality of cargo zones. More preferably, the first pressure sensor is located in a position in the uppermost cargo zone generally adjacent the accommodation area.

The first and second pressure sensors are configured to sense the respective pressures in the cargo zone and in the accommodation area, and respectively transmit the first and second pressures to the associated controller. The controller is configured to determine the difference between the first and second pressures. The controller is further preferably configured to control the operation of the one or more fans to ensure that the difference between the first and second pressures is maintained above the pressure differential. As stated above, the pressure differential is preferably at least 50 Pa, and more preferably between 50 and 100 Pa. Thus, the second pressure is preferably at least 50 Pa above the first pressure.

In an alternative embodiment, the air pressure system may comprise a differential pressure sensor. A first pressure sensing end of the differential pressure sensor may be located in, or fluidly connected with, the accommodation area of the vessel, and a second pressure sensing end of the differential pressure sensor may be located in, or fluidly connected with, the uppermost cargo zone. The first and second pressure sensing ends may be respectively fluidly connected with the accommodation area and the uppermost cargo zone by respective conduits extending from the first and second pressure sensing ends. The first and second ends of the differential pressure sensor are configured to sense the respective pressures in the accommodation area and in the uppermost cargo zone, and transmit the respective pressures to the associated controller. Similar to the above, the controller is then configured to determine the difference between the respective pressures, and control operation of the one or more fans to ensure that the pressure differential is maintained.

In an alternative embodiment, a first pressure sensing end of the differential pressure sensor may be fluidly connected with the controller or the controller integrated with the variable speed drive (VSD) via a conduit, and the second pressure sensing end may be fluidly connected to the uppermost cargo zone via a conduit extending to the uppermost cargo zone.

In a still further alternative embodiment, the air pressure system may comprise a pressure sensor located in, on, or adjacent to the one or more fans, which pressure sensor is configured to measure a resistance exerted on the one or more fans during operation. The resistance exerted on the one or more fans may be interpolated in a manner known to those skilled in the art in order to determine a pressure differential between a pressure in the accommodation area and an outside air pressure external to the accommodation area. The associated controller may be configured to control the pressure differential to ensure that the accommodation area is at a greater relative pressure than the cargo zone.

The system preferably comprises at least a first power source, independent of the ship's power. Alternatively, the system may draw its power from the ship's power. The power source is configured to provide power to at least the controller, the first and second pressure sensors, the one or more fans of the air pressure system, the one or more recirculation fans, the low-range monitoring system, and the high-range monitoring system. The air quality monitor of the low-range monitoring system (located adjacent the source of air) may alternatively be powered by another power source, such as a battery.

The system may comprise a first power source and a second power source. The second power source is preferably a back-up power source and may provide power to the components powered by the first power source in a case where the first power source becomes non-operational. The first and second power sources may be respective first and second mobile generators. Alternatively, the first and second power sources may be respective first and second batteries, or any combination of a mobile generator and a battery.

The gaseous fumigant is preferably configured to exit the cargo zones via one or more openings located upon a deck of the vessel. In a preferred embodiment, a flexible stack or chimney is located about each of the one or more openings, and is configured to direct exiting gaseous fumigant generally upwardly away from the deck of the vessel. The one or more openings may comprise a combination of mechanical ventilators, vent houses, or escape trunks.

Any of the features described in connection with other aspects set out in the Summary may also have application to this aspect.

In accordance with a second aspect, there is provided, a system for fumigating a vessel, wherein the system is ancillary to the vessel, the system comprising:

a fumigant delivery system for delivering fumigant to a
        cargo area of the vessel at one or more delivery sites;
    an air pressure system for maintaining a pressure within
        a selected area of the vessel which is greater than a
        pressure within a cargo area of the vessel, wherein an
        air intake for the air pressure system is remote from the
        one or more fumigant delivery locations and the one or
        more exhaust sites.

Preferably, the air intake is more than 30 metres from the one or more fumigant delivery locations.

An exhaust system may be provided for exhausting fumigant from the cargo area subsequent to fumigation from one or more exhaust sites; and preferably the air intake is more than 30 m from the one or more exhaust sites.

The air intake may be located quayside, outwardly of the hull of the vessel or at the forward end of the vessel.

Preferably, the air pressure system includes a controller to maintain the pressure throughout fumigation and exhaust.

Any of the features described in connection with other aspects set out in the Summary may also have application to this aspect.

2. Method of Fumigating a RORO Vessel

In another aspect, there is provided, a method of fumigating a vessel, the method comprising:

delivering fumigant to a cargo area of the vessel;
    wherein the vessel is a roll-on/roll-off vessel.

Preferably the method further includes delivering air to a selected area of the vessel above the cargo area to maintain a selected minimum pressure differential between the selected area and the cargo area, such that the pressure of the selected area is greater than the cargo area. Preferably the method further includes delivering the fumigant to the cargo area at one or more delivery sites and the method further includes exhausting fumigant from the cargo area subsequent to fumigation from one or more exhaust sites and delivering air to a selected area of the vessel to maintain a selected minimum pressure differential between the selected area and the cargo area, such that the pressure of the selected area is greater than the cargo area, wherein an air intake for the air delivery is remote from the one or more fumigant delivery locations and the one or more exhaust sites.

Preferably the air intake is more than 30 metres from the one or more fumigant delivery locations and the one or more exhaust sites. In a more preferred form of the invention, the air intake is located quayside, outwardly of the hull of the vessel or at the forward end of the vessel.

The method may further include: delivering the fumigant to fumigate the cargo area; exhausting fumigant from the cargo area subsequent to fumigation; and delivering air to a selected area of the vessel to maintain a pressure within the selected area which is greater than a pressure within the cargo area, wherein the air delivery is maintained throughout fumigation and exhaust.

Any of the features described in connection with other aspects set out in the Summary may also have application to this aspect.

3. Method of Configuring a Fumigation System

In a further aspect, there is provided, a method of configuring a system for fumigating a vessel, wherein the system is ancillary to the vessel, the method including:

configuring an air intake for an air pressure system which is operable to maintain a minimum selected pressure differential between a selected area of the vessel and a cargo area such that a pressure within the selected area of the vessel is greater than a pressure within the cargo area of the vessel, wherein the air intake is configured to draw air from the quayside or at a location outwardly beyond the hull of the vessel.

Preferably the air pressure system includes one or more fans and the method further includes configuring the fans, quayside. The air pressure system may include a variable speed drive and a controller controls speed of the one or more fans via the variable speed drive, the method further including configuring the variable speed drive, quayside.

The method may further include providing a source of fumigant for fumigating the vessel, wherein the source of fumigant is disposed quayside.

The method may further include configuring a mobile crew escape boom, quayside.

Any of the features described in connection with other aspects set out in the Summary may also have application to this aspect.

4. Control System

In accordance with yet another aspect, there is provided, a control system which is ancillary to a roll-on/roll-off vessel (RORO vessel), the ancillary control system including a controller configured to:

receive pressure or differential pressure readings from a selected area of the vessel and/or a cargo area during a fumigation, and in response to such readings, control air delivery to a selected area of the vessel in order to maintain a selected minimum pressure differential between the selected area and a cargo area with the pressure of the selected area being greater than the cargo area; and maintain the pressure differential throughout fumigation and subsequent exhaust of the fumigant from the cargo area.

Preferably the selected minimum pressure differential is at least 50 Pa, or between 50 Pa and 100 Pa. The selected minimum pressure differential may be pre-selected. The ancillary control system may be responsive to one or more pressure sensors and/or differential pressure sensors and is preferably further configured to control one or more air supply fans to supply air to the selected area to maintain the selected minimum pressure differential. The ancillary control system is preferably configured to control at least a speed of the one or more fans via a variable speed drive.

The ancillary control system may be further configured to perform low range monitoring to detect one or more of: gaseous fumigant; carbon dioxide; carbon monoxide; and other volatile organic compounds (VOCs) within the selected area and/or at an air intake for the delivered air.

Any of the features described in connection with other aspects set out in the Summary may also have application to this aspect.

In accordance with a still further aspect, there is provided, a method of pre-configuring a control system which is ancillary to a roll-on/roll-off vessel (RORO vessel), wherein the method includes pre-configuring a controller of the ancillary control system such that the controller is:

operable to receive pressure or differential pressure readings from a selected area of the vessel and/or a cargo area during a fumigation, and in response to such readings, control air delivery to a selected area of the vessel in order to maintain a selected minimum pressure differential between the selected area and a cargo area with the pressure of the selected area being greater than the cargo area; and operable to maintain the pressure differential throughout fumigation and subsequent exhaust of the fumigant from the cargo area.

Preferably the method further includes preconfiguring the ancillary control system to maintain the selected minimum pressure differential of at least 50 Pa, or between 50 Pa and 100 Pa. The method may further include preconfiguring the ancillary control system to maintain at least a pre-selected minimum pressure differential. Preferably, the method further includes preconfiguring the ancillary control system to control one or more air supply fans to deliver the air to the selected area.

The method may further include pre-configuring the ancillary control system or an additional ancillary control system to perform low-range monitoring to detect one or more of: gaseous fumigant; carbon dioxide; carbon monoxide; and other volatile organic compounds (VOCs) within the selected area and/or at an air intake for the delivered air, wherein the controller control air delivery in response to an output of the low range monitoring.

Any of the features described in connection with other aspects set out in the Summary may also have application to this aspect.

5. Temporary Bulkhead

In another aspect, there is provided, a temporary bulkhead configured to fluidly seal an entryway of a vessel, the bulkhead comprising:

a body configured to be located in an entryway of the vessel;

a seal located about the body and configured to contact the entryway to fluidly seal the entryway; and one or more openings within the body, said one or more openings being adapted to connect with fluid conduits.

The body with the seal is preferably dimensioned to be larger than an opening of the entryway.

The openings in the body preferably include engagement features to facilitate connection to the fluid conduits.

The one or more openings may be configured to allow for the passage of fluid through the bulkhead. The fluid may be gaseous fluid. The bulkhead may include one or more other openings configured to allow for the passage of power, data, and/or other services through the bulkhead.

At least some of the one or more openings include respective valves.

Preferably the bulkhead is configured to be sealingly connected to one or more air conduits as set out above in connection with the foregoing aspects.

The bulkhead preferably forms part of the above described systems for fumigating a vessel. Any of the features described in connection with other aspects set out in the Summary may also have application to this aspect.

As used herein, except where the context requires otherwise, the term "comprise" and variations of the term, such as "comprising", "comprises" and "comprised", are not intended to exclude further additives, components, integers or steps.

Further aspects and further embodiments of the aspects described in the preceding paragraphs will become apparent from the following description, given by way of example and with reference to the accompanying drawings.

DETAILED DESCRIPTION OF THE EMBODIMENTS

Typical RORO Vessel

Figure 1:
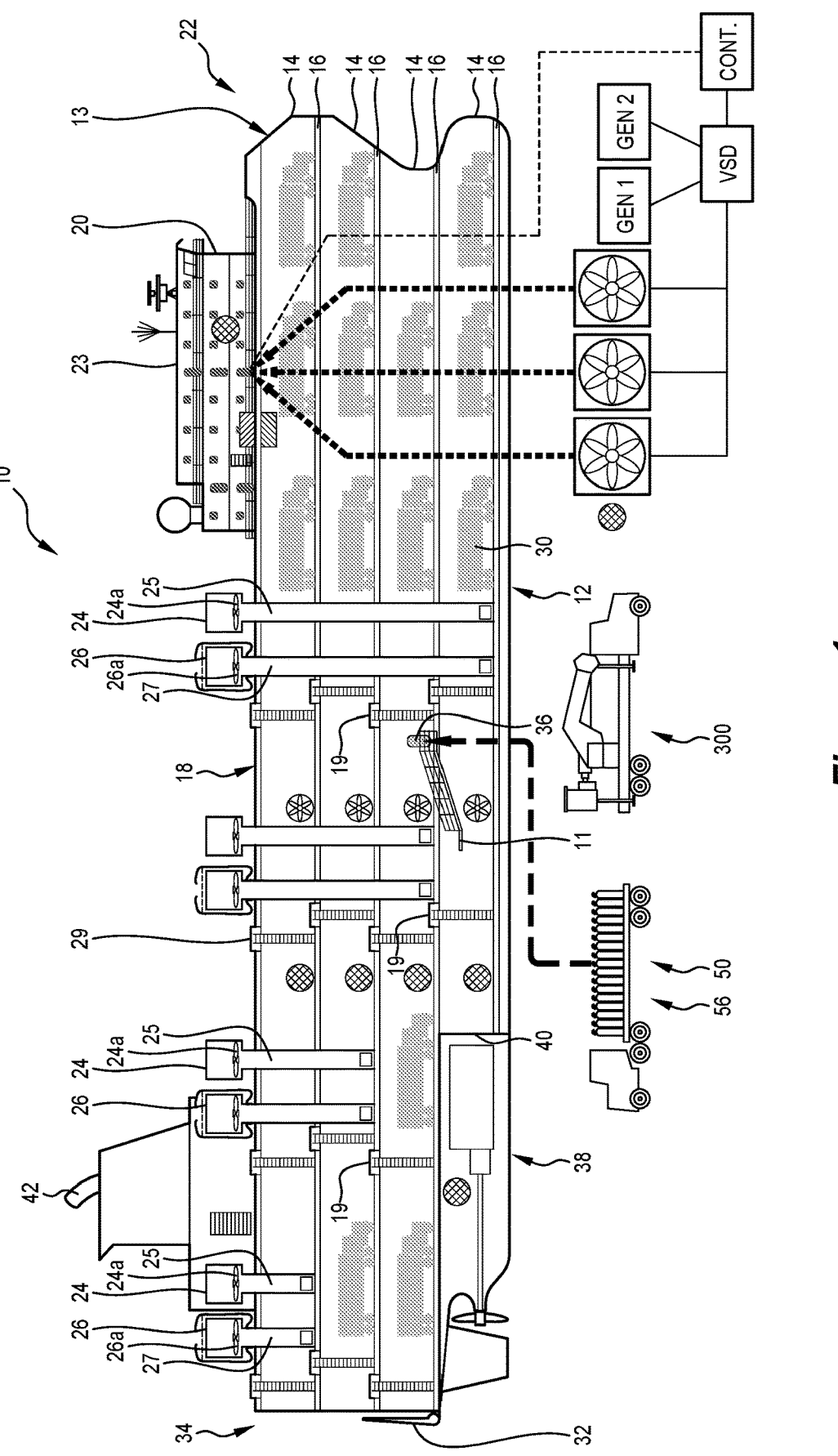
FIG. 1 is a side cross-sectional view of a RORO vessel that may be fumigated according to an embodiment and shows a fumigant delivery system, an air pressure system, and a temporary flexible exhaust according to an embodiment, and illustrates a fumigation operation.

Referring to FIG. 1, there is a shown a roll-on/roll-off vessel 10 (hereafter "RORO vessel") that comprises a hull 12 and a cargo area 13 comprising plurality of separate cargo zones 14. Each of the cargo zones 14 are water-tight or gas-tight and include respective cargo decks 16. As is illustrated in FIG. 1, each cargo zone 14 includes a single cargo deck 16. However, it will be appreciated that the RORO vessel illustrated in FIG. 1 is merely exemplary, and that a RORO vessel may include more than one cargo deck 16, such as two or three cargo decks, in each separate cargo zone 14. A typical RORO vessel may include a total of 13 cargo decks distributed amongst four separate cargo zones. Each of the cargo decks within a single cargo zone are typically interconnected by ramps.

The RORO vessel 10 further comprises a weather deck 18 located above an uppermost one of the plurality of cargo zones 14 and an accommodation area 20 located upon the weather deck 18 generally adjacent a fore end 22 of the vessel 10. The accommodation area 20 is arranged to provide accommodation to the crew or personnel of the vessel 10 and includes the various living quarters of the vessel 10. A bridge 23 is located above the accommodation area 20 and is generally fluidly connected thereto. The bridge 23 houses the various controls, navigation instrumentation, and other equipment necessary for the commanding of the vessel 10.

The cargo zones 14 of the RORO vessel 10 are located one above the other and extend substantially along the entire length of the vessel 10. In the illustrated embodiment, the vessel 10 includes four such cargo zones 14. As is described above, each of the cargo zones 14 is configured to be water-tight or gas-tight, and is further connectable to an adjacent cargo zone 14 via one or more moveable or sealable ramps. The moveable ramps are moveable between an open position and a closed position. In the open position, a ramp connecting adjacent cargo zones 14 enables the passage of crew members, other personnel, and cargo between the adjacent connected cargo zones 14. As will be appreciated, in the open position, the adjacent connected cargo zones 14 are fluidly connected to one another such that, for example, gaseous fumigant in one cargo zone 14 is able to flow into the adjacent connected cargo zone 14. In the closed position however, the ramp acts as a seal between adjacent cargo zones 14 such that the adjacent cargo zones are water-tight or gas-tight.

The uppermost cargo zone 14 may be accessed by crew or other personnel, such as specially trained fumigation personnel, via one or more escape trunks located in the weather deck 18. The RORO vessel 10 illustrated in FIG. 1 includes between 8 and 10 such escape trunks located generally around the perimeter of the weather deck 18 (only 4 escape trunks are illustrated in FIG. 1). The escape trunks define respective openings or entryways into the uppermost cargo zone 14 via the weather deck 18, and include ladders or a combination of ladders and stairways that extend downwardly through each cargo deck 16 to the lowermost cargo deck 16 in the lowermost cargo zone 14.

Figure 5:
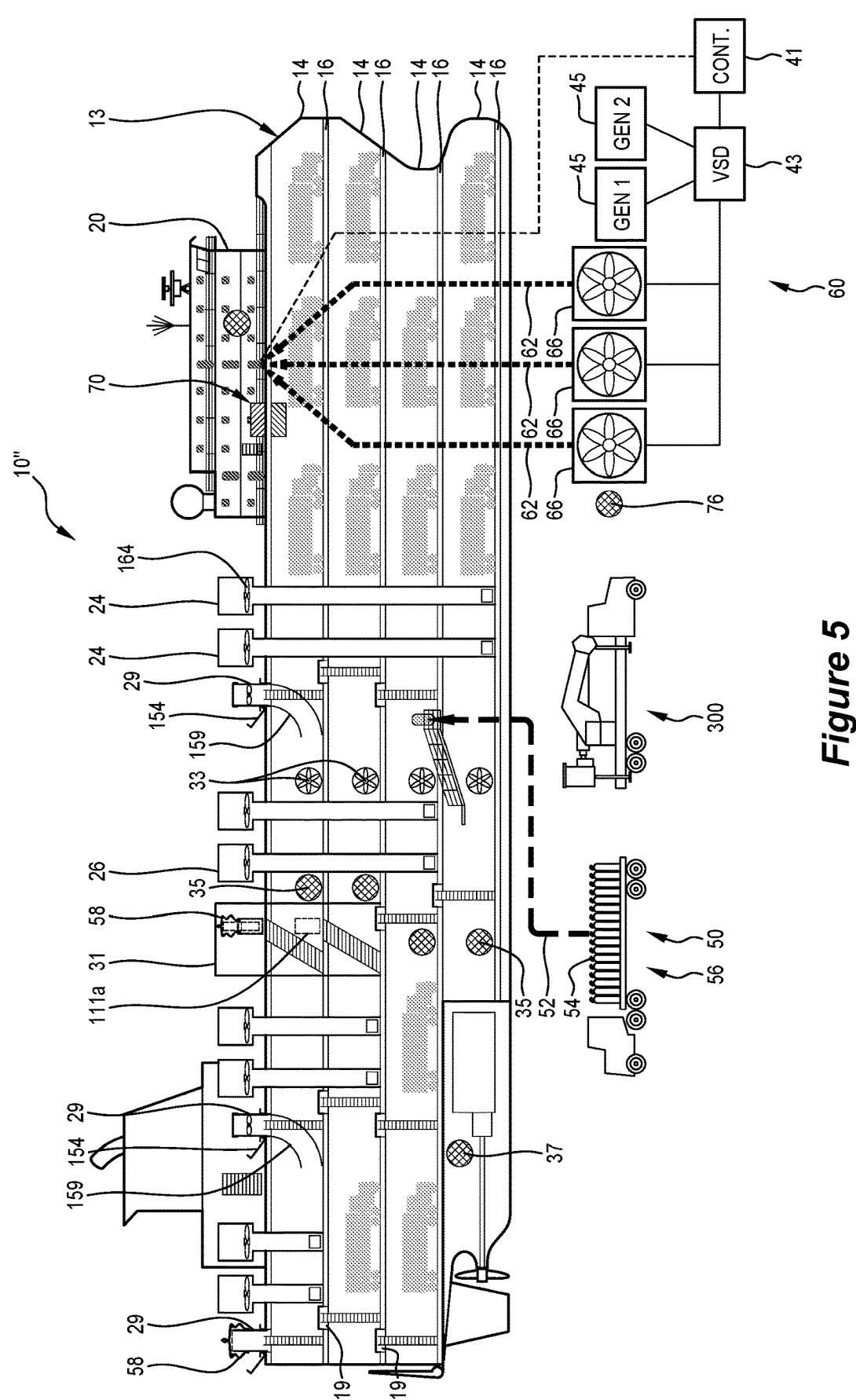
FIG. 5 is a side cross-sectional view of an alternative RORO vessel that may be fumigated according to an embodiment and shows a fumigant delivery system, an air pressure system, and a temporary flexible exhaust according to an embodiment, and illustrates a fumigation operation.

The opening or entryway into the uppermost cargo zone 14 via the weather deck 18 may be in the form of a hatch 29 (see FIG. 1 for example) or a stairway 31 (see FIG. 5 example). Additionally, the escape trunks define hatches 19 and/or stairways located throughout the cargo area 13. The hatches 19 and/or stairways connect adjacent cargo decks 16 within a cargo zone 14, and connect adjacent cargo zones 14. The hatches 19 define respective hatch openings that may be selectively closed as desired to fluidly seal a cargo zone 14 from an adjacent cargo zone 14. The stairways include respective doors at an upper end and a lower end thereof that may also be selectively closed as desired to fluidly seal a cargo zone 14 from an adjacent cargo zone 14. As is described below, during the fumigation operation and the subsequent ventilation operation, each of the hatches 19 and/or stairways that connect adjacent cargo zones 14 are closed, but for the hatches 19 and/or stairways of a single escape trunk which is selected as a "riser" to enable various services, such as conduits containing gaseous fumigant, to be routed throughout the cargo area 13. For the reasons described below, it is preferred that the escape trunk that is located generally closest to the midship of the vessel 10 is selected as the riser. For convenience, this particular escape trunk will be hereafter referred to as "the riser escape trunk". To enable the routing of services, such as conduits containing gaseous fumigant, throughout the cargo area 13, each of the hatches 19 of the riser escape trunk are fitted with a hatch bulkhead 115 (see FIG. 16), and each of the doors of each stairway of the riser escape trunk are fitted with a door bulkhead 111 (see FIG. 15). As is described above, each stairway includes an upper door and a lower door. FIG. 1 shows various internal hatches 19 in the cargo area 13 that, if used as the riser escape trunk, would be fitted with the hatch bulkhead 115. FIG. 5 shows an internal door 111a in the cargo area 13, that if used as the riser escape trunk, would be fitted with the door bulkhead 111. The hatch bulkheads 115 and the door bulkheads 111 are described in detail below.

The RORO vessel 10 illustrated in FIG. 1 includes a plurality of escape trunks in the form of hatches 29 that include ladders only. FIG. 5 illustrates an alternative RORO vessel 10''' that includes a plurality of escape trunks in the form of hatches 29 and stairways 31, wherein at least one escape trunk includes a combination of ladders and stairways. Specifically, it can be seen in FIG. 5 that the second right-most escape trunk includes a combination of stairways and ladders.

Mechanical Supply Ventilators and Exhaust Ventilators

The vessel 10 further comprises a plurality of supply mechanical ventilators 24 and a plurality of exhaust mechanical ventilators 26. Specifically, each cargo zone 14 includes respective dedicated supply and exhaust mechanical ventilators 24, 26. Each of the supply mechanical ventilators 24 are configured to supply fresh air from about the weather deck 18 into their respective cargo zones 14 via respective ducts 25 extending from the weather deck 18 to the respective cargo zone 14 (as illustrated by the direction of the arrows in FIG. 2). Each of the exhaust mechanical ventilators 26 are configured to exhaust air from their respective cargo zones 14 via respective ducts 27 into the atmosphere above the weather deck 18 (as illustrated by the direction of the arrows in FIG. 2). Although FIG. 1 illustrates that each cargo zone 14 includes a single supply mechanical ventilator 24 and a single exhaust mechanical ventilator 26 only, a person skilled in the art will appreciate that each of the cargo zones 14 will typically include a plurality of supply and exhaust mechanical ventilators. Each of the supply and exhaust mechanical ventilators 24, 26 are selectively closeable and openable as desired to respectively control the supply and exhaust of air to and from the cargo zones 14. Furthermore, each of the supply mechanical ventilators 24 include respective fans 24a configured to assist with moving air into the cargo zones 14, as desired. Alternatively, air may be passively drawn into the cargo zones 14 via the supply mechanical ventilators 24. Each of the exhaust mechanical ventilators 26 include respective fans 26a configured to assist with removing air from the cargo zones 14, as desired.

As is further illustrated in FIG. 1, located upon each of the decks 16 of the cargo zones 14 is cargo 30. The cargo 30 may be any form of cargo, and is typically wheeled or tracked cargo that is rolled onto or driven into the cargo zones 14 of the vessel 10 via a selectively openable stern ramp 32 located at the aft end 34 of the vessel 10. After loading of the cargo 30 and during operation of the vessel 10, access to the cargo zones 14 can be achieved via an accommodation ladder landing water-tight door 36 adjacent a gangway 11 in a starboard side of the hull 12. As is described above, the uppermost cargo zone 14 may also be accessed via the one or more escape trunks (either in the form of hatches 29 or staircases 31) in the weather deck 18. As is illustrated throughout the figures, the accommodation ladder landing water-tight door 36 provides direct access to the second lowermost cargo zone 14. It will be appreciated however, that on other RORO vessels, the accommodation ladder landing water-tight door may provide direct access to another cargo zone other than the second lowermost cargo zone.

The vessel 10 further comprises a engine room 38 located adjacent a lowermost one of the plurality of cargo zones 14 generally adjacent the aft end 34 of the vessel. The engine room 38 is physically separated from the lowermost cargo zone 14 via a vertically extending plate-steel bulkhead 40, and is further separated from the second lowermost cargo zone 14 by a plate-steel flooring of the second lowermost cargo zone 14. As will be appreciated, the engine room 38 houses the engines and other associated equipment used to power and propel the vessel 10, and is controlled by the various controls located in the bridge 23. Crew members may be located in the engine room 38 from time-to-time during operation of the vessel 10 and potentially during fumigation and subsequent ventilation. Exhaust gases produced during use of the engines is exhausted via a smoke-stack or chimney 42 located upon the weather deck 18 generally adjacent the aft end 34 of the vessel 10.

A travel tower 300 is located quay side to provide an alternative means of embarkment or disembarkment of the RORO vessel 10 during an emergency or fumigation operation when access to the RORO vessel 10 via the accommodation ladder water-tight door 36 is not possible. The travel tower 300 is a cherry picker style vehicle that is capable of raising passengers from the quay to the weather deck 18 of the RORO vessel 10.

It will be appreciated that the RORO vessel 10 illustrated in FIG. 1 and described above is merely exemplary and that the particular form and arrangement of the RORO vessel may be varied without affecting the scope of the invention.

Ancillary Fumigation System

As is described above, there is a present need to ensure that the cargo 30 in the vessel 10 is properly fumigated prior to unloading, whilst ensuring the safety of the crew of the vessel and any specially trained fumigation personnel. To this end, the present disclosure provides a system and method for fumigating a vessel, embodiments of which are illustrated in FIGS. 1 to 28 and described in detail below.

Referring initially to FIG. 1, there is shown a fumigant delivery system 50 for delivering fumigant to the cargo zones 14 of the vessel 10, and an air pressure system 60 for maintaining a pressure within the accommodation area 20 greater than a pressure within the cargo area 13. Accordingly, by maintaining a greater relative pressure in the accommodation area 20 compared to the cargo area 13, any gaseous fumigant located within the cargo area 14 is prevented from entering the accommodation area 20 via, for example, unintended openings or cracks in the plate-steel flooring beneath the accommodation area 20.

The fumigant delivery system 50 comprises a plurality of first conduits 52 (shown schematically in FIG. 1) connected at their respective first ends to fumigant-containing gas cylinders 54 stored in a mobile vehicle 56 located quayside of the vessel 10. Typically, the gas cylinders are arranged into separate groups. Each of gas cylinders in a group may be fluidly connected via a manifold. Two first conduits may extend from each manifold and deliver gaseous fumigant into a respective cargo zone 14. The fumigant delivery system may typically comprise between 20 and 36 first conduits 52. Each of the first conduits 52 may have a diameter of between approximately ¼ inch (6.35 mm) to 1 inch (25.4 mm). However, the preferred diameter of the each of the conduits 52 is ⅜ inch (9.53 mm).

The fumigant may be any one or more of a pesticide, insecticide, disinfectant, purifier, bactericide, decontaminant, antiseptic, sanitiser, vaccine, anti-viral, or vapour, and may comprise any one or more of sulfuryl fluoride, ethyl formate, ethane dinitrile, formaldehyde, methyl bromide, chloropicrin, iodoform, hydrogen cyanide (blue fume), nitrogen, and carbon dioxide. While the disclosure includes reference to sulfuryl fluoride, it will be appreciated that other fumigants may be incorporated into the embodiments. Additionally, modes of delivery and levels of fumigant detected by the high range detection system and the low range detection system may vary according to the selected fumigant.

A second end of each of the plurality of first conduits 52 is fluidly connected to the cargo zones 14 via a fumigation bulkhead 110 located in the accommodation ladder landing water-tight door 36. The fumigation bulkhead 110 (see FIGS. 13 and 14), described in detail below, is configured to fluidly seal the accommodation ladder landing water-tight door 36 to ensure that any gaseous fumigant delivered to the cargo zones 14 via the plurality of first conduits 52 is prevented from escaping the cargo zones 14 into the environment through the accommodation ladder landing water-tight door 36.

Figure 16:
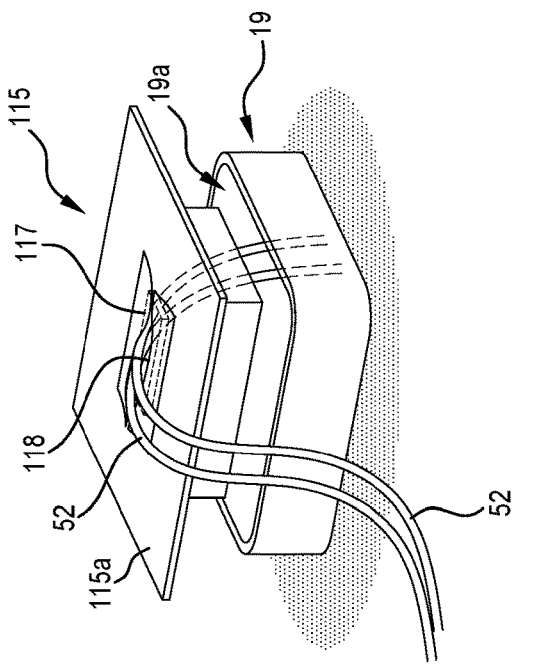
FIG. 16 is a side perspective view of a hatch bulkhead associated with the fumigant delivery system of FIG. 1 and to be used internally throughout the cargo area.

In addition to the fumigation bulkhead 110 located in the accommodation ladder landing water-tight door 36, a plurality of other bulkheads are located throughout the cargo area 13. As is described above, there is a hatch bulkhead 115 (FIG. 16) located at each hatch 19 connecting adjacent cargo zones 14 in the riser escape trunk. Additionally, there is a door bulkhead 111 (FIG. 15) at each door of each staircase connecting adjacent cargo zones 14 in the riser escape trunk, such as at door 111a shown in FIGS. 5 and 6. The door bulkhead 111 is generally rectangular in overall form and includes a seal 84 configured to seal the respective door opening. The door bulkhead 111 also includes a general rectangular opening 113 in a lower half thereof, which opening 113 is configured to receive a plurality of the first conduits 52 to thereby deliver the gaseous fumigant across the bulkhead 111. The hatch bulkhead 115 (FIG. 16) is generally square in cross-section and is dimensioned to be larger than the generally square hatch opening 19a. Thus, the hatch bulkhead 115 is configured to fluidly seal the hatch 19 by sitting over and covering the hatch opening 19a. It is noted that FIG. 16 illustrates an exploded view in which the hatch bulkhead 115 is located partially above the opening 19a in the hatch 19. Similar to the door bulkhead 111, the hatch bulkhead 115 includes a generally rectangular opening 117 which is configured to receive a plurality of the first conduits 52 to thereby deliver the gaseous fumigant across the hatch bulkhead 115.

The combination of the fumigation bulkhead 110, the door bulkheads 111, and the hatch bulkheads 115 used throughout the cargo area 13 enable the entire cargo area 13 to be fumigated substantially simultaneously, or alternatively, allow for a particular cargo zone 14 to be fumigated separately of any other cargo zone 14, or further alternatively, allow for a plurality of cargo zones 14 to be fumigated separately of any other cargo zone 14.

Mode of Fumigation

Fumigating the entire cargo area 13 substantially simultaneously is achieved in the following manner. Firstly, a plurality of first conduits 52 are fluidly connected at their first ends to the mobile fumigant-containing vehicle 56, and fluidly connected at their second ends to an external side of the fumigation bulkhead 110 located in the accommodation ladder landing water-tight door 36. Then, another plurality of first conduits 52 are connected at their first ends to the internal side of the fumigation bulkhead 110, and connected at their second ends to respective recirculation fans 33 located in the second lowermost cargo zone 14 (as is described above, the accommodation ladder landing water-tight door 36 provides direct access to the second lowermost cargo zone 14). The recirculation fans 33 are configured to disperse the gaseous fumigant throughout the second lowermost cargo zone 14. There are preferably two recirculation fans 33 located in each cargo deck 16 in each cargo zone 14 in order to disperse the gaseous fumigant throughout each cargo zone 14. In a preferred arrangement, there is a first fan 33 located generally at midship on a starboard side of the vessel 10, and a second fan located generally at midship on a port side of the vessel 10. The first and second fans 33 preferably face in opposite directions within the vessel 10. For example, the first fan 33 may face towards an aft end of the vessel 10, and the second fan 33 may face towards a fore end of the vessel 10 in order to disperse the gaseous fumigant fully throughout each cargo zone 14.

Each of the recirculation fans 33 are preferably direct drive axial fans. Preferably, each of the recirculation fans 33 are 7.5 kW direct drive axial fans. Further, each of the recirculation fans 33 preferably have a diameter of 760 mm, and a centreline located 1.5 m above the cargo deck 16 to ensure sufficient dispersion of the gaseous fumigant throughout each cargo deck 16. The recirculation fans 33 may have an air volume flow rate of between approximately 4 to 16 m³/s. The preferred air volume flow rate of the recirculation fans 33 is approximately 10 m³/s.

In order to fumigate cargo zones other than the second lowermost cargo zone 14, another plurality of first conduits 52 are connected at their first ends to the internal side of the fumigation bulkhead 110, and connected at their seconds ends to recirculation fans 33 located in each of the other cargo zones 14. The plurality of first conduits 52 may be routed to a particular cargo zone 14 through one or more of the door bulkheads 111 (FIG. 15) and/or through one or more of the hatch bulkheads 115 (FIG. 16) in the escape trunk riser. As is described above, the door bulkheads 111 and the hatch bulkheads 115 include respective openings 113 and 117 through which the first conduits 52 may be routed. In this manner, a plurality of the first conduits 52 may extend from the internal side of the fumigation bulkhead 110 located in the accommodation ladder landing water-tight door 36 to recirculation fans 33 in each of the cargo zones 14 to thereby substantially simultaneously fumigate the entire cargo area 13 whilst creating separation between the cargo zones 14.

Figure 15:
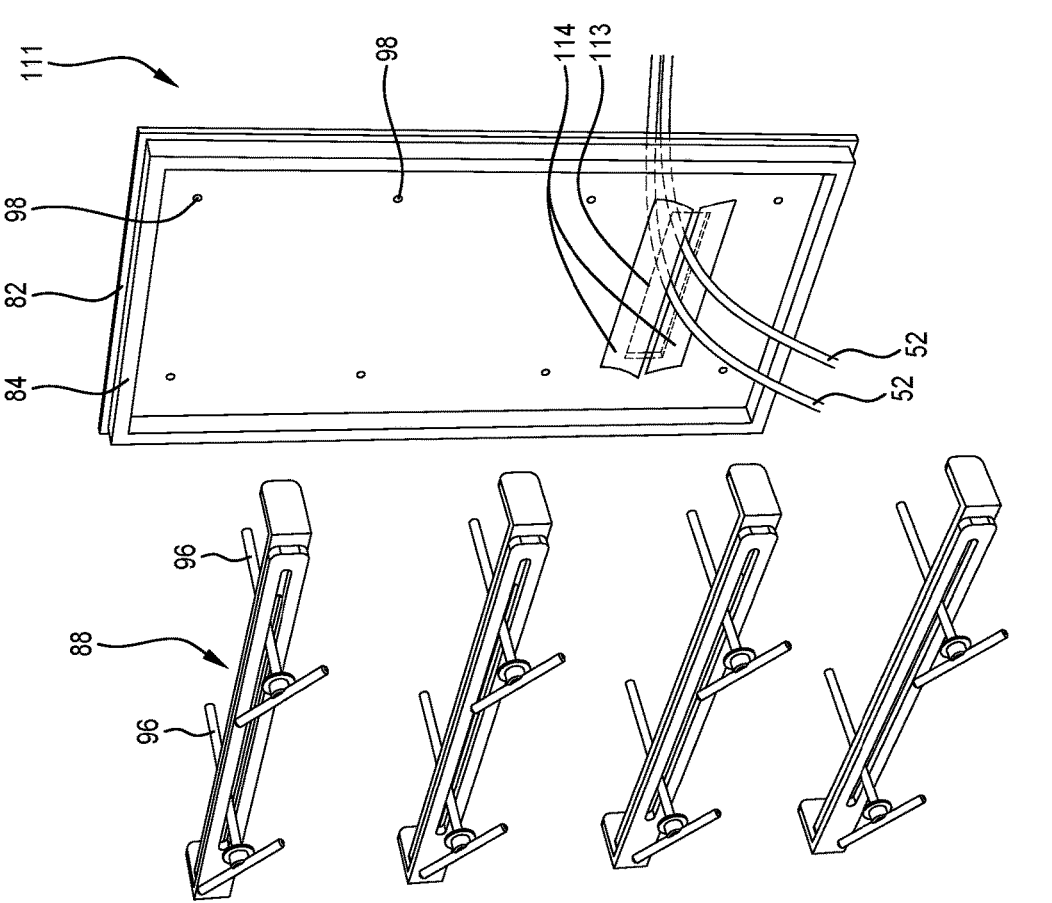
FIG. 15 is a side perspective view of another bulkhead associated with the fumigant delivery system of FIG. 1 and to be used internally throughout the cargo area.

To fumigate a single cargo zone 14 only, or a particular plurality of cargo zones 14 only, a plurality of the first conduits 52 are connected at their first ends to the internal side of the fumigation bulkhead 110, and connected at the second ends to the recirculation fans 33 in the particular cargo zone 14 or cargo zones 14 which are desired to be fumigated. Any particular cargo zone 14 which is not desired to be fumigated is fluidly sealed by closing the openings 113 and 117 in the respective door bulkheads 111 and hatch bulkheads 115 that lead into that cargo zone 14 via the escape trunk riser. As is shown in FIG. 15, the door bulkhead 111 includes includes a pair of flaps 114 located about the opening 113 and which are configured to close and fluidly seal the opening 113. The flaps 114 preferably comprise a rubber sealing material and are biased to a closed position in which the flaps 114 close the opening 113. Similarly, as is shown in FIG. 16, the hatch bulkhead 115 includes a flap 118 located about the opening 117 and which is configured to close and fluidly seal the opening 117. The flap 117 is similar to the pair of flaps 114 and comprises a rubber sealing material biased to a closed position. In this manner, by fluidly sealing particular cargo zones 14 by closing the openings 113 and 117 in the respective door bulkheads 111 and hatch bulkheads 115 leading into those cargo zones 14 from the escape trunk riser, one or more of the cargo zones 14 may be separately fumigated as desired.

As is shown in FIGS. 15 and 16, two first conduits 52 extend through the door bulkhead 111 and/or the hatch bulkhead 115 in order to fumigate each cargo zone 14. A person skilled in the art would appreciate however that a different number of conduits 52 may be used to fumigate each particular cargo zone 14. For example, two to four conduits 52 may be used to fumigate each cargo deck 16 in a cargo zone 14, and one or two conduits 52 may be connected to each recirculation fan 33 on each cargo deck 16. In the illustrated arrangement, two first conduits 52 are used to fumigate each cargo zone 14. A first one of the conduits 52 is connected to the first fan 33 located in the particular cargo zone 14, and a second one of the conduits 52 is connected to the second fan 33 located in a particular cargo zone 14. As is described above, the escape trunk that is located generally closest to the midship of the vessel 10 is selected as the riser escape trunk through which services, such as the conduits 52, are routed throughout the entire cargo area 13. Advantageously, this positioning allows for the shortest possible conduits 52 to be used throughout the cargo area 13 as the fumigation bulkhead 110 is also located generally at the midship of the vessel 10, as are the recirculation fans 33 in each cargo zone 14.

High-Range Monitoring System

Other features of the fumigation system 50 will now be described. Referring back to FIG. 1, in order to determine the efficacy of the fumigation operation, a high-range monitoring system is used. The high-range monitoring system comprises a plurality of sensors 35 located in each of the cargo zones 14. The sensors 35 detect gaseous fumigant in the form of sulfuryl fluoride in a range of concentrations from about 5,000 ppm to 15,000 ppm. The sensors 35 in the high-range monitoring system feedback to a controller 41. The high-range monitoring system may be operated during fumigation and ventilation.

During the fumigation operation, the supply and exhaust mechanical ventilators 24, 26 are maintained in a closed position to prevent the escape of gaseous fumigant into the environment above the weather deck 18. Attached about each of the exhaust mechanical ventilators 26 are respective flexible temporary exhausts 58, described in detail below. The flexible temporary exhausts 58 assist with the safe removal of the gaseous fumigant from the cargo zones 14 after the fumigation operation has been completed. In the embodiment illustrated in FIG. 1, the temporary flexible exhausts 58 are shown in a non-operational deflated position owing to the exhaust mechanical ventilators 26 being in a closed or non-operational position.

Overpressure in Crew Areas

As is described above, during the fumigation operation, the air pressure system 60 is configured to maintain an air pressure within the accommodation area 20 greater than an air pressure within the cargo zones 14. In the illustrated embodiment, the bridge 23 is also maintained a greater relative pressure than the cargo zones 14 due to the bridge 23 being fluidly connected to the accommodation area 20.

The air pressure system includes three second conduits 62 (shown schematically in FIG. 2) configured to deliver air to the accommodation area 20 of the vessel 10. Each of the conduits 62 is connected at their first ends to a source of air located quayside of the vessel 10, i.e. remotely of the vessel 10, and connected at their second ends to an accommodation bulkhead 80 (FIG. 7), described below, located in an entryway 64 into the accommodation area 20. The accommodation bulkhead 80 is configured to be fluidly connected to each of the three conduits 62 to thereby deliver the air into the accommodation area 20, and is further configured to fluidly seal the entryway 64 to prevent air from escaping via the entryway 64. During the fumigation operation, the accommodation area 20 is preferably substantially hermetically sealed, or at least hermetically sealed to a sufficient extent, to prevent the escape of relatively significant amounts of air from the accommodation area 20 that would otherwise make it difficult to maintain the accommodation area 20 at a greater relative pressure compared to the cargo zones 14. To this end, during the fumigation operation, any vents or openings into the accommodation area are preferably closed and any air conditioning systems that supply and/or remove air from the accommodation area 20 are preferably shutdown.

Figure 2:
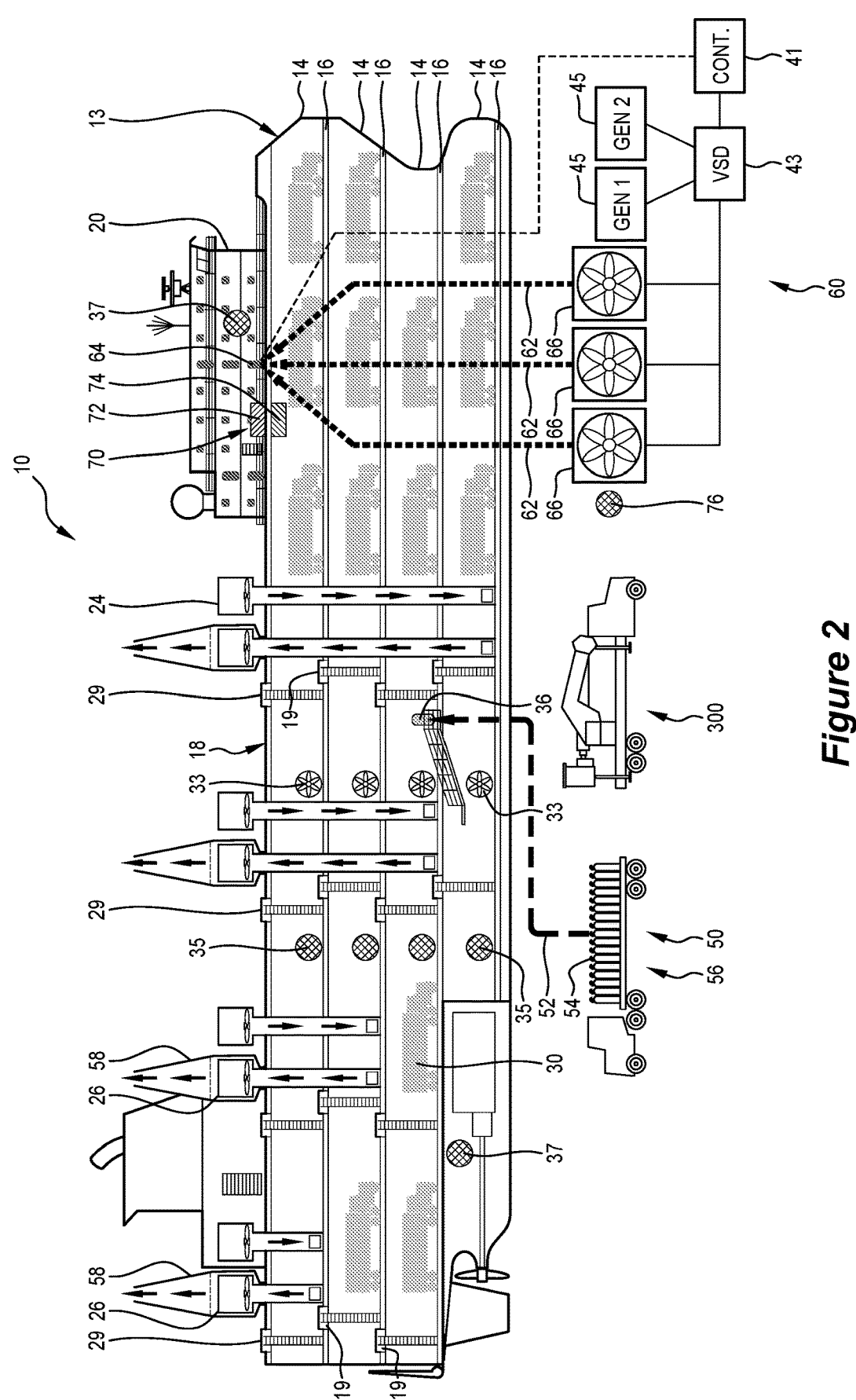
FIG. 2 is similar to FIG. 1, but shows a ventilation operation (which occurs after the fumigation operation)

As is illustrated in FIG. 2, each of the first ends of the conduits 62 are connected to a respective fan 66 configured to draw air into the respective conduit 62 such that the air can be delivered to the accommodation area 20 via the respective conduit 62. The fans 66 are controlled by the controller 41 which at least controls a speed of the fans 66 via a variable speed drive (VSD) 43 to thereby adjustably control a volume rate of air delivered to the accommodation area 20 via each of the conduits 62. The VSD 43 and fans 66 are powered by first and second mobile generators 45. Preferably, the second generator 45 acts a back-up power source for the first generator 45 in a case where the first generator 45 becomes non-operational.

Differential Pressure Sensing

The air pressure system 60 further includes a differential pressure sensor 70 that includes a first pressure sensing end 72 located in the accommodation area 20 of the vessel, and a second pressure sensing end 74 located in the uppermost cargo zone 14 and adjacent the accommodation area 20. The first and second ends 72, 74 of the differential pressure sensor 70 are configured to sense the respective pressures in the accommodation area 20 and in the uppermost cargo zone 14, and transmit the respective pressures to the controller 41. The controller 41 is configured to determine a difference between the respective pressures, and to control the operation of the fans 66 connected to the conduits 62 to ensure that a predetermined desired pressure differential is maintained. Preferably, the pressure in the accommodation area 20 is maintained at least 50 Pa above the pressure in the cargo zone 14. More preferably, the pressure in accommodation area 20 is maintained between 50 and 100 Pa above the pressure in the cargo zone 14. As will be appreciated by those skilled in the art, if the pressure differential decreases below the predetermined desired pressure differential, the controller controls the fans 66 via the VSD 43 to increase the speed of the fans 66 to thereby increase the volume flow rate of air drawn into the accommodation area 20 via the conduits 62. Conversely, if the pressure differential increases above a maximum desired pressure differential, the controller controls the fans 66 via the VSD 43 to decrease the speed of the fans 66 to thereby decrease the volume flow rate of air drawn into the accommodation area 20 via the conduit 62.

Air Quality Monitoring

The air pressure system 60 further includes an air quality monitor 76 located quayside generally adjacent the fans 66 (and thus the intake ends of the conduits 62). The air quality monitor is configured to detect the presence of one or more of gaseous fumigant, carbon dioxide, carbon monoxide, and other volatile organic compounds (VOCs), and may report the presence of these gases to the controller and/or to an operator so that the air pressure system 60 may be shutdown if required. The air quality monitor 76 forms part of a low-range monitoring system which is used to detect fumigant gas comprising sulfuryl fluoride in the range of 0.5 ppm-230 ppm, with a resolution of 0.1 ppm. Other sensors 37 forming part of the low-range monitoring system may be used in specific locations to detect gas leaks. For example, sensors 37 may be located in the engine room 38, passageways and crew access and accommodation area 20. The sensors 37 may be daisy-chained with cable feeds fed back to the control system. The low-range monitoring system is operated during fumigation and ventilation.

The fumigation operation may last for several hours, such as around 12 to 48 hours or longer depending upon the treatment requirements. Throughout the fumigation operation, the air pressure system 60 is operated to maintain the predetermined desired pressure differential between the accommodation area 20 and the cargo zones 14, and is optionally operated beyond the end of the fumigation operation, at least until clearance of the gaseous fumigant from the cargo zones 14 and the cargo 30.

Ventilation Operation

After the fumigation operation has been completed, a ventilation operation is commenced in order to safely remove the gaseous fumigant from the cargo zones 14 and the cargo 30. The ventilation operation may last for several hours, such as around 10 to 36 hours or so. During the ventilation operation, the supply mechanical ventilators 24 are opened and their associated fans 24a are operated in order to enable a fresh supply of air to be drawn into the cargo zones 14. Additionally, the exhaust mechanical ventilators 26 are opened and their associated fans 26a are operated in order to positively remove air containing the gaseous fumigant from the cargo zones 14. This ventilation operation is illustrated in FIG. 2. As can be seen in FIG. 2, during the ventilation operation, the flexible temporary exhausts 58 are in a generally upright operational position in order to expel air containing the gaseous fumigant generally upwardly away from the weather deck 18. As is described below, the flexible temporary exhausts 58 extend above the accommodation area 20 when in the operational position to ensure, as best as possible, that the escaping gaseous fumigant is directed away from the accommodation area 20.

Bulkheads

FIGS. 7-14 provide details relating to the fumigation bulkhead 110 located at the accommodation ladder landing water-tight door 36, the accommodation bulkhead 80 located in the entryway 68 into the accommodation area 20, and details relating to the flexible temporary exhausts 58 and other potential ventilation methods.

Figure 7:
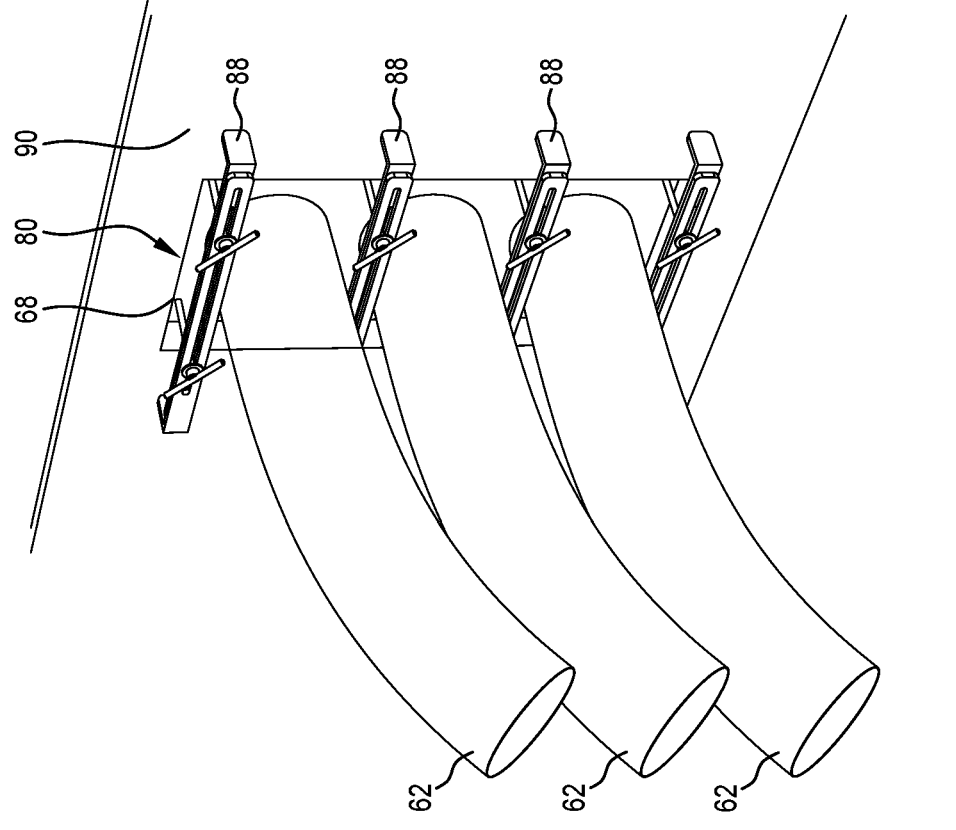
FIG. 7 is a front-side perspective view of a portion of an accommodation area of the vessel of FIG. 2, and further illustrates a temporary bulkhead and other components of the air pressure system of FIG. 2.
Figure 10:
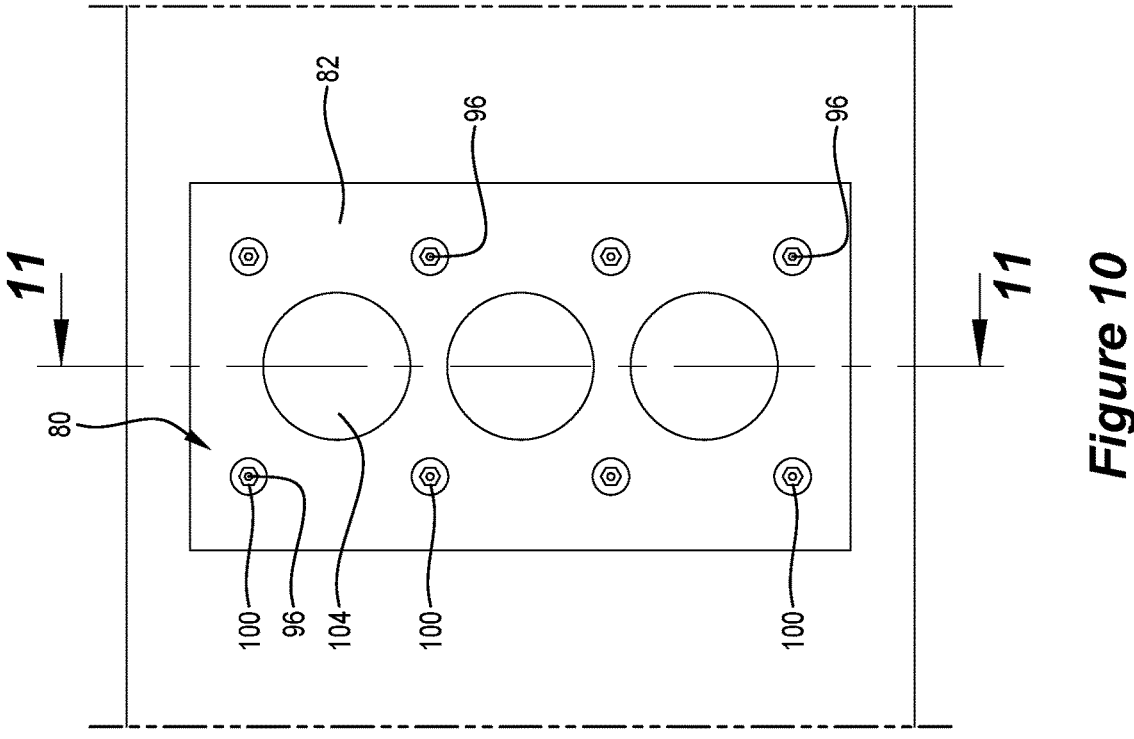
FIG. 10 is a front-on view of the bulkhead of FIG. 7.

Referring initially to FIG. 7, there is illustrated a temporary bulkhead 80 located at the starboard entryway 68 into the accommodation area 20. Each of the three conduits 62 of the air pressure system 60 are fluidly and sealingly connected to the accommodation bulkhead 80 in order to deliver the air through the accommodation bulkhead 80 into the accommodation area 20.

Figure 8:
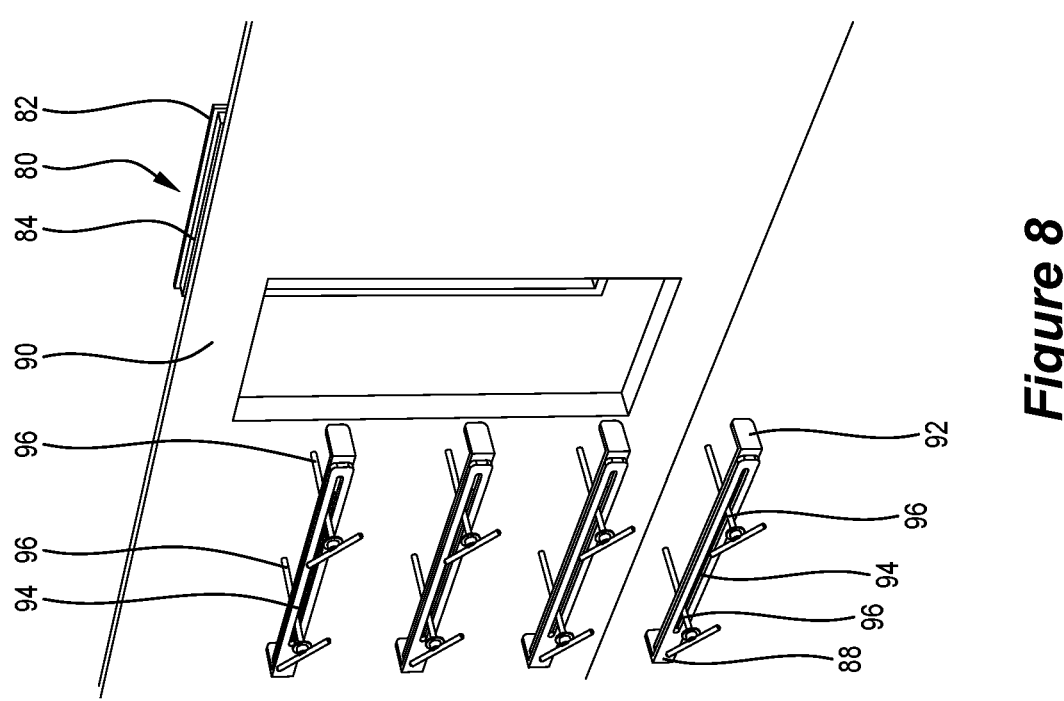
FIG. 8 is similar to FIG. 7, but only shows some components of the temporary bulkhead.
Figure 9:
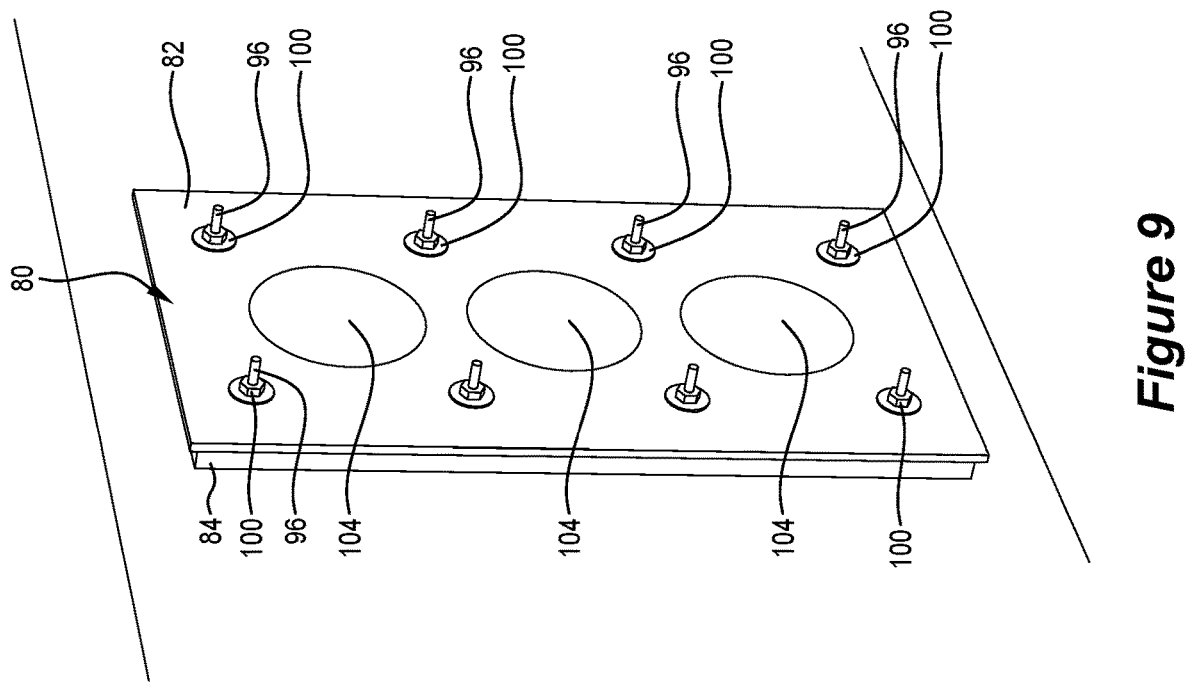
FIG. 9 is similar to FIG. 8, but is a rear-side perspective view.
Figure 12:
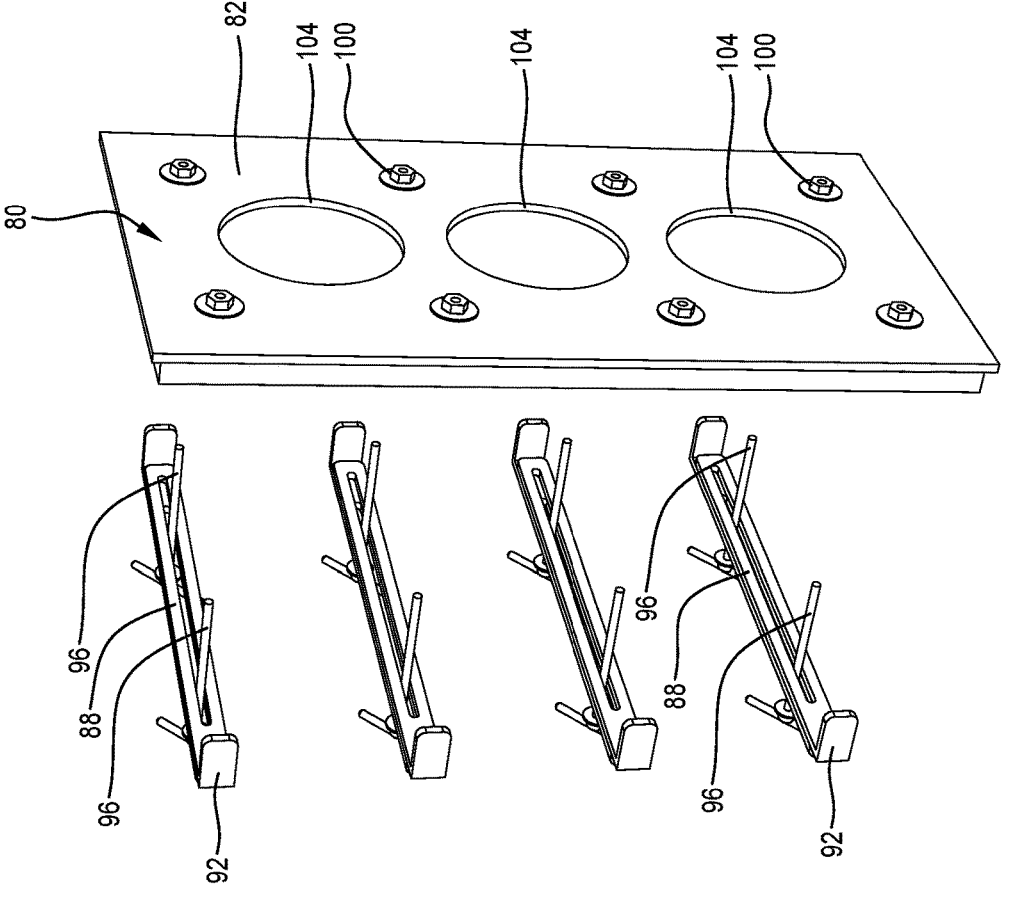
FIG. 12 is a rear-side perspective view of the bulkhead of FIG. 8.
Figure 11:
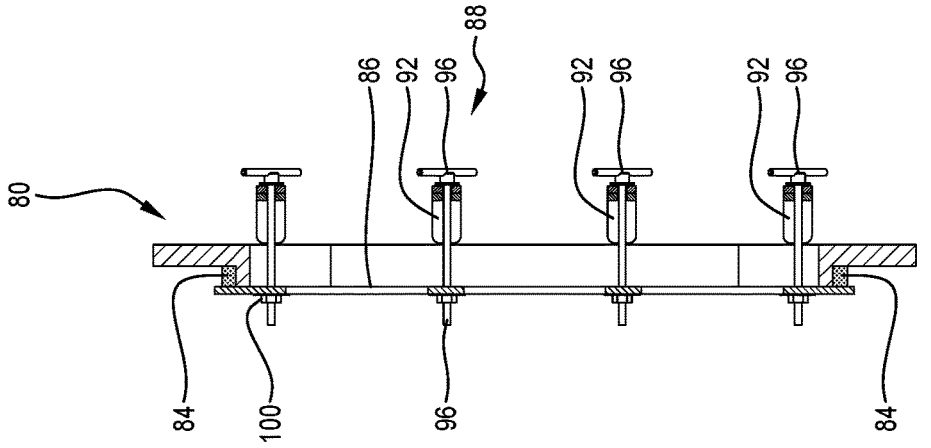
FIG. 11 is a side cross-sectional view of the bulkhead of FIG. 10 along the line

Referring to FIGS. 8 and 9, the temporary accommodation bulkhead 80 is installed by firstly positioning the bulkhead 80 in the entryway 68 at an internal side of the accommodation area 20 (the internal side shown in FIG. 9). The bulkhead 80 comprises a rectangular body 82 (FIG. 9) that is dimensioned to be slightly larger than the generally rectangular opening of the entryway 68. The bulkhead 80 further comprises a seal 84 (FIG. 9) on a first, or outer, face 86 of the body 82. The seal 84 is generally rectangular in cross-section throughout its length and extends along the perimeter of the rectangular body 82 on the outer face 86, and is slightly inset from the outer edges of the body 82 (see FIGS. 9 and 11). The outer face 86 of the body 82 is positioned to face away from the internal side of the accommodation area such that the seal 84 contacts and seals against the opening in the entryway 68. The accommodation bulkhead 80 is maintained in this position by a series of generally rectangular brackets 88 (FIG. 7) secured against an outer wall 90 of the accommodation area 20 surrounding the entryway 68.

Referring to FIG. 8, accommodation bulkhead 80 includes four generally rectangular brackets 88 configured to be disposed generally horizontally across the entryway 68. Each of the brackets 88 includes outer flanged longitudinal ends 92 that protrude laterally and which are configured to contact the outer wall 90 of the accommodation area 20. Each of the brackets 88 further includes an elongate opening or slit 94 extending substantially along the entire length of the brackets 88. The elongate opening 94 is configured to receive a pair of generally T-shaped tubular rods 96. The distal ends of the rods 96 are configured to be received in respective generally circular apertures 98 (FIG. 15) extending through the body 82 of the bulkhead 80 such that the distal ends of the rods 96 protrude from the inner face of the body 82 (FIG. 9). Respective nuts 100 are located about each of the distal ends of the rods 96 in order to secure the position of the rods 96 with respect to the body 82 of the bulkhead 80. The proximal ends of the rods 96 include respective generally circular plates (FIG. 8) which are dimensioned to be wider than the elongate opening 94 and which are therefore configured to contact the bracket 88 to adjust the position of the brackets 88 with respect to the body 82. As will be appreciated by a person skilled in the art, the generally T-shaped proximal ends of the rods 96 may be rotated by hand in order to adjust the position of the rods 96 with respect to the body 82 of the bulkhead 80, and thus adjust the position of the seal 84 against the opening in the entryway 68. For example, during tightening, the generally circular plate 102 of the rod 96 contacts the outer surface of the bracket 88 in order to move the bracket 88 relatively toward the body 82 of the bulkhead 80.

As is shown in FIGS. 9 to 12, the body 82 of the bulkhead 80 includes three generally circular openings 104 arranged vertically one above the other along a transverse centreline of the body 82, and extending through the body 82. Each of the openings 104 is configured to be fluidly and sealingly connected to a respective one of the second conduits 62 of the air pressure system 60. The openings 104 may include respective valves (not shown) that may operate as one-way valves that enable air to enter the accommodation area 20 via the openings 10, but prevent any backflow of air.

Figure 14:
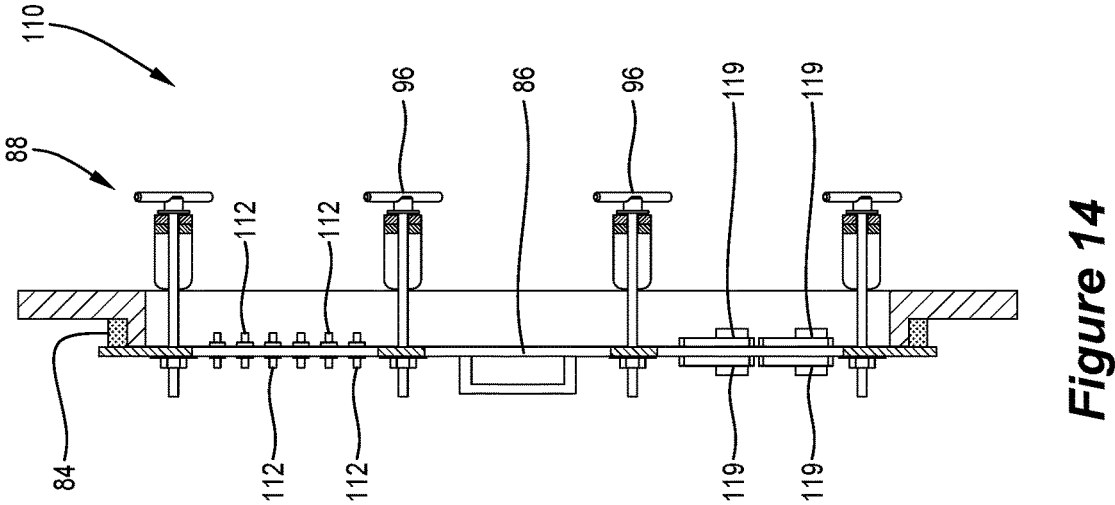
FIG. 14 is a side cross-sectional view of the bulkhead of FIG. 13.
Figure 13:
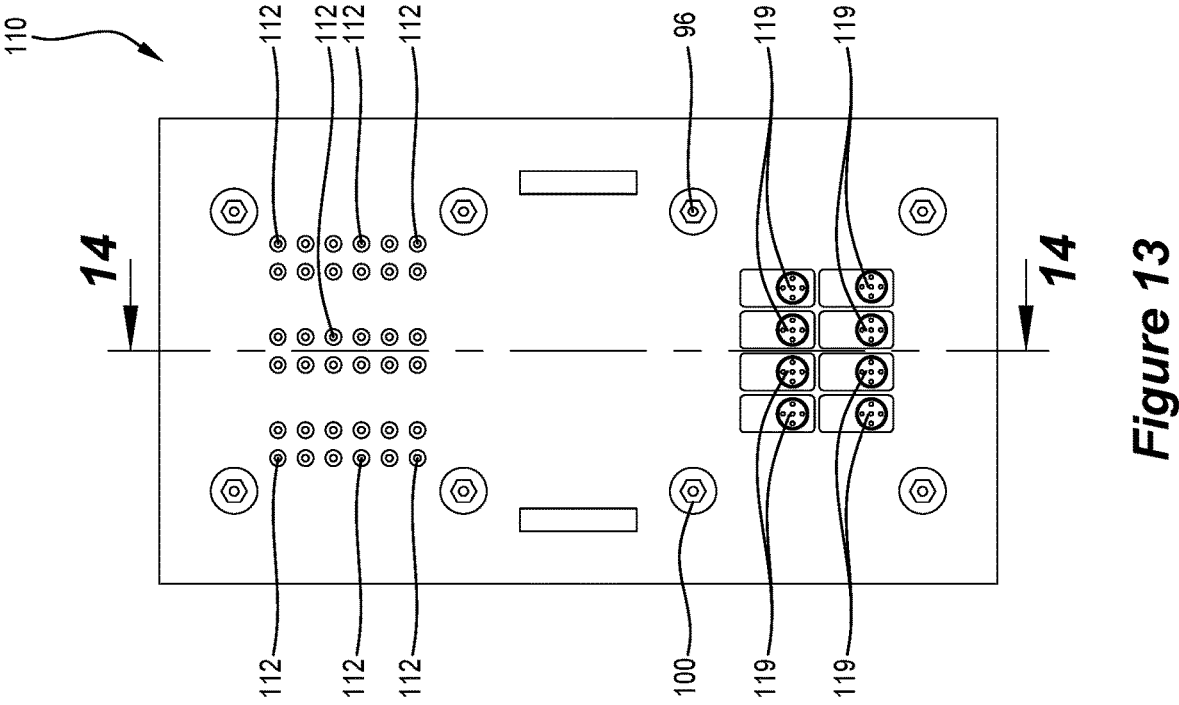
FIG. 13 is a rear front-on view of another bulkhead associated with the fumigant delivery system of FIG. 1.

FIGS. 13 and 14 illustrate the temporary fumigation bulkhead 110 that is configured to be located at the accommodation ladder landing water-tight door 36. It will be appreciated however that the fumigation bulkhead 110 may instead be fitted at any other suitable opening into the cargo area 13, such as at a door leading into a staircase (escape trunk) 31 (FIG. 5) on the weather deck 18 or via the rear stern access door. However, the fumigation bulkhead 110 is preferably fitted to the accommodation ladder landing water-tight door due to its generally central location within the cargo area 13.

The fumigation bulkhead 110 is similar in form and operation to the accommodation bulkhead 80. For example, similar to the accommodation bulkhead 80, the fumigation bulkhead 110 includes a body 82, a generally rectangular seal 84 extending generally about the perimeter of the body 82 on an outer face 86 of the body 82, a plurality of brackets 88 and associated T-shaped tubular rods 96, a plurality of generally circular apertures 98 extending through the body 82 of the bulkhead 110 configured to receive the distal ends of the tubular rods 96, and respective nuts 100 located about each of the distal ends of the rods 96 on the inner face of the body 82 in order to secure the rods 96 to the body 82. Additionally, the fumigation bulkhead 110 is sealed against the accommodation ladder landing water-tight door 36 in substantially the same manner as the accommodation bulk-head 80 is sealed against the opening 64 into the accom-modation area 20. However, the fumigation bulkhead 110 is externally fitted to the accommodation ladder landing water-tight door 36, whereas the accommodation bulkhead 80 is internally fitted to the opening 64 into the accommodation area 20.

The fumigation bulkhead 110 also includes a plurality of generally circular openings or spigots 112 located generally in an upper half of the body 82, and which are configured to be fluidly and sealingly connected to respective first con-duits 52 of the fumigation system 50 in order to deliver gaseous fumigant across the bulkhead 110. Specifically, the fumigation bulkhead 110 includes 36 openings or spigots 112 arranged in three adjacent vertically extending groups, each group including 6 rows of two openings 112 arranged side-by-side. Thus the fumigation bulkhead 110 can up to receive 36 first conduits 52 from the mobile fumigant-containing vehicle 56, and can distribute 36 first conduits 52 throughout the cargo area 13. As is shown in FIG. 14 for example, the openings or spigots 112 extend through the bulkhead 110 to be connected to respective first conduits 52 on either side of the bulkhead 110. It will be appreciated that the fumigation bulkhead 110 could include any number of openings or spigots 122 as required according to the par-ticular vessel to be fumigated. In general, the fumigation bulkhead 110 will include enough openings or spigots 112 to enable two to four conduits 52 to be routed to each cargo deck 16.

The fumigation bulkhead 110 also includes a series of ports 119 located generally in a lower half of the body 82, and which are configured to receive power and/or data and transmit the power and/or data across the bulkhead 110. In the illustrated embodiment, the fumigation bulkhead 110 includes eight ports 119 arranged in two rows, one above the other. As is described above, it will be appreciated that the fumigation bulkhead 110 could include any number of ports 119 as required according to the particular vessel to be fumigated. In general, the fumigation bulkhead 110 will include enough ports 119 to enable at least one 3-phase power cable to be routed to each cargo deck 16. Each port 119 is preferably configured to supply a current of between 15 to 50 Amps.

The ports 119 may provide power to the recirculation fans 33 in each of the cargo zones 14, and may also provide a data connection between the sensors 35 of the high-range moni-toring system and the controller 41. Specifically, one or more power cables may be connected between the first and/or second mobile generators 45 to the ports 119 on the external side of the fumigation bulkhead 110, and one or more other power cables may be connected between the ports 119 on the internal side of the fumigation bulkhead 110 and the recir-culation fans 33 located in each of the cargo zones 14. The sensors 35 of the high range monitoring system may be connected to the controller 41 in a similar manner.

As is described above, FIGS. 15 and 16 respectively illustrate the door bulkheads 111 located in each door of each staircase in the riser escape trunk, and the hatch bulkheads 115 located in each hatch 19 in the riser escape trunk. The door bulkhead 111 is generally similar in form to the accommodation bulkhead 20 and the fumigation bulkhead 110, and is sealed about each door of each staircase in the riser escape trunk in generally the same manner that the accommodation bulkhead 80 and the fumigation bulkhead 110 are sealed to their respective openings 64 and 36. Specifically, each of the door bulkheads 111 include a plurality of circular apertures 98 configured to receive the tubular rods 96, and so forth. The hatch bulkhead 115 comprises a generally square plate-like body 115a that is larger in each dimension when compared to the generally rectangular hatch opening 19a. In this way, when located against the hatch opening 19a, the plate-like body acts to seal the opening 19a. Each hatch opening 19a is generally 900 mm×900 mm, or 1000 mm×1000 mm.

Fumigants

As stated above, different fumigant chemicals may be used which may require a variation on the fumigant delivery method described. As will be appreciated by the skilled person, fumigation chemicals such as ethyl formate, ethane-dinitrile, and hydrogen cyanide can be flammable under certain conditions and concentrations that may be encoun-tered if the above described method is used.

In the method above, this is most likely to occur during the vaporisation of the chemical from a liquid to a gas as the concentration of the fumigant will pass through the flam-mable region. This change in concentration occurs when introducing the fumigant to the recirculation fans 33 in the cargo zone 14 of the RoRo vessel 10. To avoid the risk of a fire starting in the cargo zones 14, an alternative method of fumigant delivery may be used for fumigant gases that present this risk.

It may be possible to safely perform a fumigation with a potentially flammable fumigant using the method for sulfuryl fluoride as described above. For example, liquid ethyl formate may be delivered to the cargo zone 14 via the plurality of first conduits 52 connected to the fumigant-container cylinders 54 of the mobile fumigation-containing vehicle 56 and one or more temporary bulkheads 110. The ethyl formate is supplied to a pump near to a recirculation fan 33 in the cargo zone 14. The pump increases the pressure of the ethyl formate to between 7 bar and 300 bar, and preferably about 200 bar. The liquid ethyl formate may be expelled from the pump via a nozzle or restriction and into the air flow path of the recirculation fans 33. Due to the high pressure of the liquid ethyl formate it leaves the nozzle at a high velocity and is atomised into a fine spray, mist or fog. The atomised liquid ethyl formate is subjected to a decrease in pressure which causes the liquid ethyl formate to change into a gaseous state and disperse into the air. The air volume supplied by the recirculation fan 33 is such that the concentration of the ethyl formate rapidly drops below the flammable range. Using this method, the risk of a fire due to combustion of the fumigant may be low as only a small part of the atomised stream exiting the conduits 52 may be in the flammable range for a short period of time.

In an alternative fumigation delivery method, potentially flammable fumigant is directed to the cargo zone 14 under fumigation in liquid form via a plurality of conduits 52 in a similar manner to that described above. However, the liquid fumigant is not directed to the recirculation fans 33, instead it is directed to mixing equipment consisting of a vaporiser or heat exchanger and a high volume mixing apparatus located near the recirculation fans. The vaporiser or heat exchanger typically consist of a coil of copper tube in a hot water or thermal oil bath however many other suitable types of heat exchanger exist. As the liquid fumigant passes through the copper coil it is warmed and transitions from a liquid to a gas. The vaporisers are typically 1 kW to 15 kW, and preferably 10 kW in power. The gaseous fumigant is then directed into a high volume mixing apparatus which draws in air and fumigant at the ratio required to create the desired fumigant concentration. The speed at which the mixing occurs is such that the flammable concentration of the fumigant is rapidly by-passed. The air/fumigant mix exits the mixing apparatus near the recirculation fans 33 so as to be evenly distributed around the cargo zone 14 under fumigation. Alternatively, the vaporised fumigant is delivered directly to the recirculation fans 33 to be mixed rather than entering the high volume mixing apparatus.

In another alternative fumigation delivery method, the mixing equipment is located on the quayside and not in the cargo zone 14 of the RORO vessel 10 to be fumigated. The fumigant is vaporised in the vaporiser or heat exchanger and mixed with air in the high volume mixing apparatus. The gaseous air/fumigant mix is then delivered to the cargo zone 14 under fumigation via flexible ducts and a temporary bulkhead configured to accommodate the flexible ducts in a similar manner to the air pressure system 60 described in detail above.

It is possible that the liquid fumigant does not require vaporisation using the vaporiser located in the cargo zone 14 or on the quay. In this instance, the liquid fumigant can be vaporised inside the high volume mixing apparatus located either in the cargo zone 14 or on the quay side. Alternatively, the liquid fumigant can be pressurised with a pump and then ejected from a nozzle to create an atomised spray, mist, or fog that can be mixed with air on the quay side. The fumigant is either delivered to the cargo zone 14 as a liquid as described above, or as a gaseous air/fumigant mix via flexible ducts as described above.

In another embodiment the gaseous air/fumigant mix can be delivered to the cargo zone 14 to be fumigated via the ducts 25, 27 which connect the cargo zone 14 to the supply mechanical ventilator 24 or exhaust mechanical ventilators 26 on the weather deck 18 of the RoRo vessel 10. The gaseous air/fumigant mix may be prepared in any manner previously described or may be delivered to the ducts 25, 27 or mechanical ventilators 24, 26 as a liquid and vaporised inside the mechanical ventilator 24, 26 or ducts 25, 27.

In a further alternative method, the fumigant may be mixed to the desired concentration quayside with a non-flammable gas other than air such as carbon dioxide or nitrogen and then delivered to the cargo zone 14 to be fumigated via flexible ducts in a similar manner to the air pressure system 60 or the mechanical ventilators 24, 26 as described above.

It may also be desirable to mix the fumigant to the desired concentration with liquid carbon dioxide and deliver the fumigant mix to the cargo zone 14 as a low temperature liquid which could then be safely vaporised using a vaporiser, heat exchanger, or atomisation as described above.

It will be appreciated by those skilled in the art that a combination of the above described fumigation methods could be utilised based on the configuration of the vessel and the fumigation to be conducted.

Temporary Flexible Exhausts

The remaining figures provide detail relating to the flexible temporary exhaust that is configured to assist with removing the gaseous fumigant from the cargo zones 14 during the ventilation operation.

Type I Temporary Flexible Exhaust

Referring initially to FIGS. 17 to 20, there is shown a flexible temporary exhaust 58 (type I) disposed about a exhaust mechanical ventilator 26. As is stated above, the flexible temporary exhaust 58 is configured to assist with removing the gaseous fumigant from the cargo zones 14 during the ventilation operation (after the fumigation operation is completed).

Figures 17, 18:
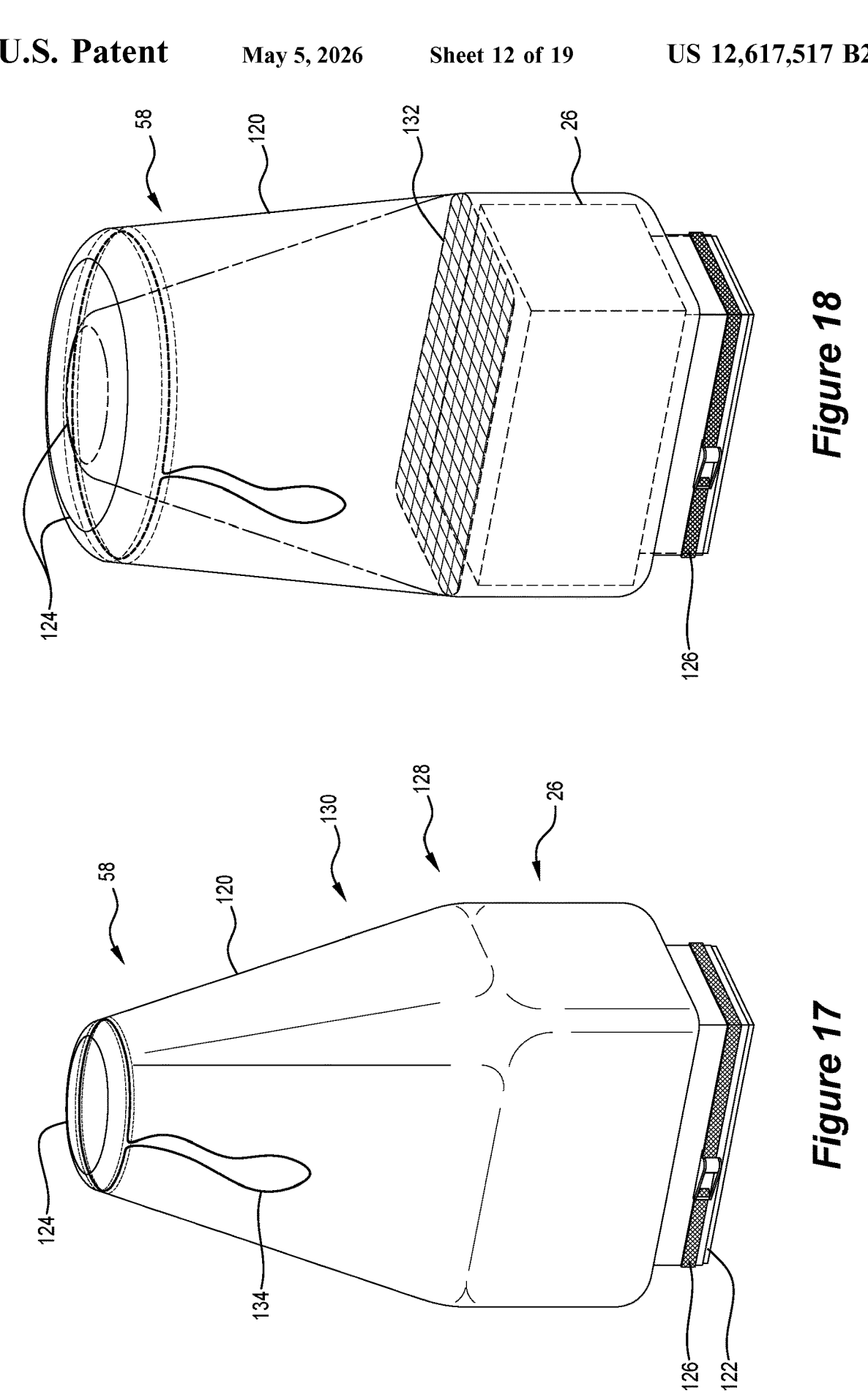
FIG. 17 is a perspective view of a flexible temporary exhaust according to an embodiment.
FIG. 18 is similar to FIG. 17, but is a cut-away view.

Referring to FIG. 17 initially, the temporary flexible exhaust 58 comprises an inflatable conduit 120 which inflates substantially vertically during use to provide an upright exhaust. The temporary flexible exhaust 58 is configured to be inflated by the exhausted air (containing the gaseous fumigant) from the cargo zones 14. The inflatable conduit 120 includes a first opening 122 at a lower end thereof, and a second opening 124 at an upper end thereof. As is illustrated in FIG. 17 for example, the second, or upper, opening 124 may have a smaller cross-sectional area than the first, or lower, opening 122 during use.

The first opening 122 is fitted over an an exhaust mechanical ventilator 26 (or a similar conduit could be fitted over a vent house, described below) and is mechanically secured thereto via a length-adjustable flexible strap 126. Once the first, or lower, opening 122 is secured to the mechanical ventilator 26 via the strap 126, the flexible exhaust 58 is in fluid communication with the mechanical ventilator 26, and is thus configured to exhaust the air exhausted from the mechanical ventilator 26 via the upper opening 124, which is located downstream of the lower opening 122 (as is shown by the direction of the arrows in FIG. 20).

As is shown in these figures, the flexible exhaust 58 is substantially conical when in use and inflated, and includes a lower generally cylindrical portion 128 (which appears somewhat rectangular in FIGS. 17 and 18 owing to flexible conduit 120 conforming to the rectangular cross-sectional shape of the mechanical ventilator 26). The flexible exhaust 58 further includes an upper generally frustoconical portion 130.

Referring to FIG. 17, the first opening 122 of the inflatable conduit 120 is fitted about a base of the mechanical ventilator 26 below the vents of the mechanical ventilator 26. During use, this positioning of the flexible exhaust 58 creates a plenum chamber beneath the vents to thereby assist with inflation of the flexible exhaust 58.

Figure 20:
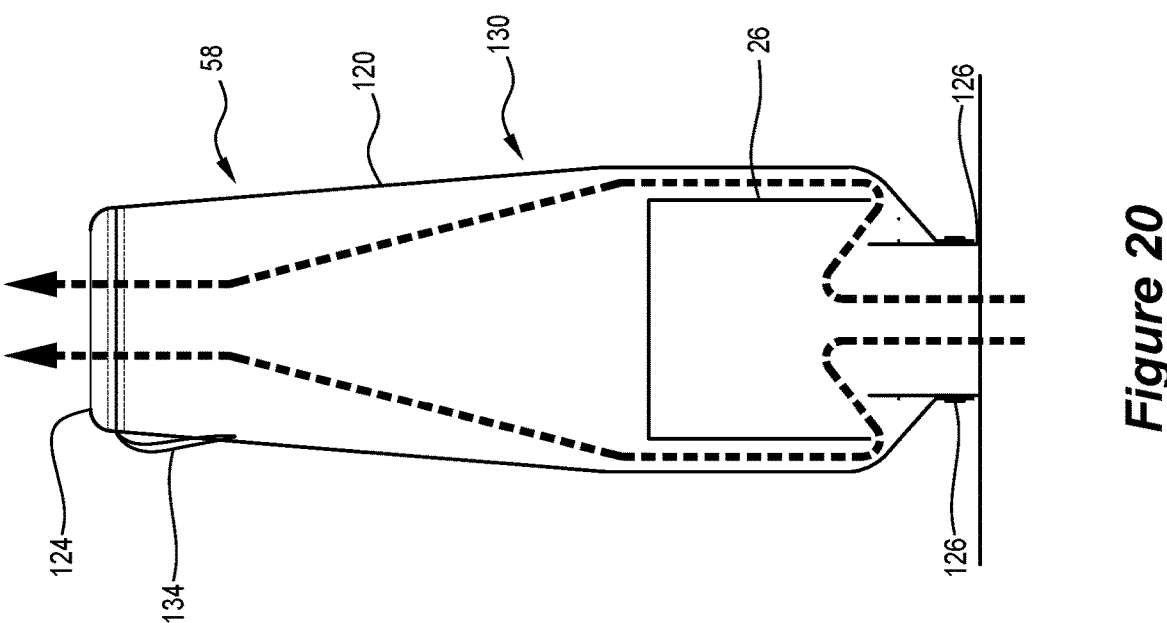
FIG. 20 is a side cross-sectional view of the flexible temporary exhaust of FIG. 19 along the line 20-20.
Figure 19:
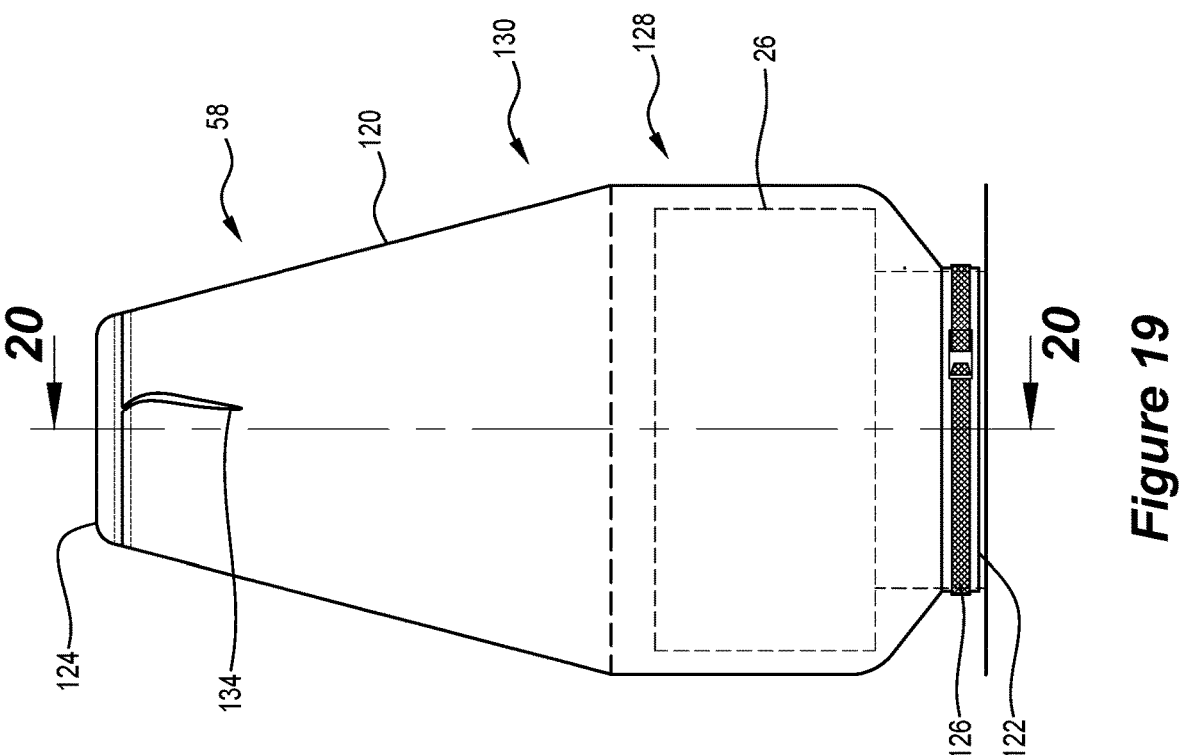
FIG. 19 is a front-on cut-away view of the flexible temporary exhaust of FIG. 17.

As is shown in FIGS. 17 to 18, the inflatable conduit 120 is sized to accommodate the mechanical ventilator 26, and preferably in such a way that gap is created between the housing of the ventilator 26 and the inflatable conduit 120 during use (as is particularly shown in FIGS. 19 and 20). The gap between an inner side wall of the inflatable conduit 120 and the ventilator housing 26 is preferably approximately 300 mm on each side of the ventilator housing 26. The inflatable conduit 120 is sized to have a height which exceeds the height of the accommodation area 20. Thus, in use, the inflatable conduit 120 has a height between approximately 8 to 10 metres. As is described above, the relatively higher positioning of the upper downstream opening 124 of the flexible exhaust 58 ensures, as best as possible, that the exhausted air (containing gaseous fumigant) is directed away from the accommodation area 20.

The particular ventilation arrangement, such as the number of mechanical ventilators 26 employed may depend upon a large variety of factors such as the design of the RORO vessel, the ventilation requirements for the particular kind of cargo and fumigant and a safe level of dilution as determined by the cargo, fumigant and relevant regulations, the flow capacity of each mechanical ventilator 26, and the zoning arrangements of the cargo decks 16. Prevailing wind another conditions may also have a bearing on the ventilation requirements. These factors can be taken into account in designing a suitable ventilation plan for a particular vessel concerned.

In one embodiment of a ventilation arrangement, illustrated in FIG. 2 and FIGS. 17 to 20, respective flexible temporary exhausts 58 are located about each exhaust mechanical ventilator 26 and assist with exhausting air containing the gaseous fumigant from the cargo zones 14. As is described above, during the ventilation operation, the supply mechanical ventilators 24 and their associated fans 24a are operated to draw in fresh air into the cargo zones 14, and the exhaust mechanical ventilators 26 and their associated fans 26a are operated to remove air containing gaseous fumigant from the cargo zones 14 via the flexible temporary exhausts 58. As is shown in FIG. 1, during the fumigation operation, the flexible temporary exhausts 58 are attached to respective exhaust mechanical ventilators 26 but are tied at their downstream openings in order to prevent the escape of gaseous fumigant into the atmosphere above the weather deck 18 during fumigation.

Type II Temporary Flexible Exhaust

Figure 21:
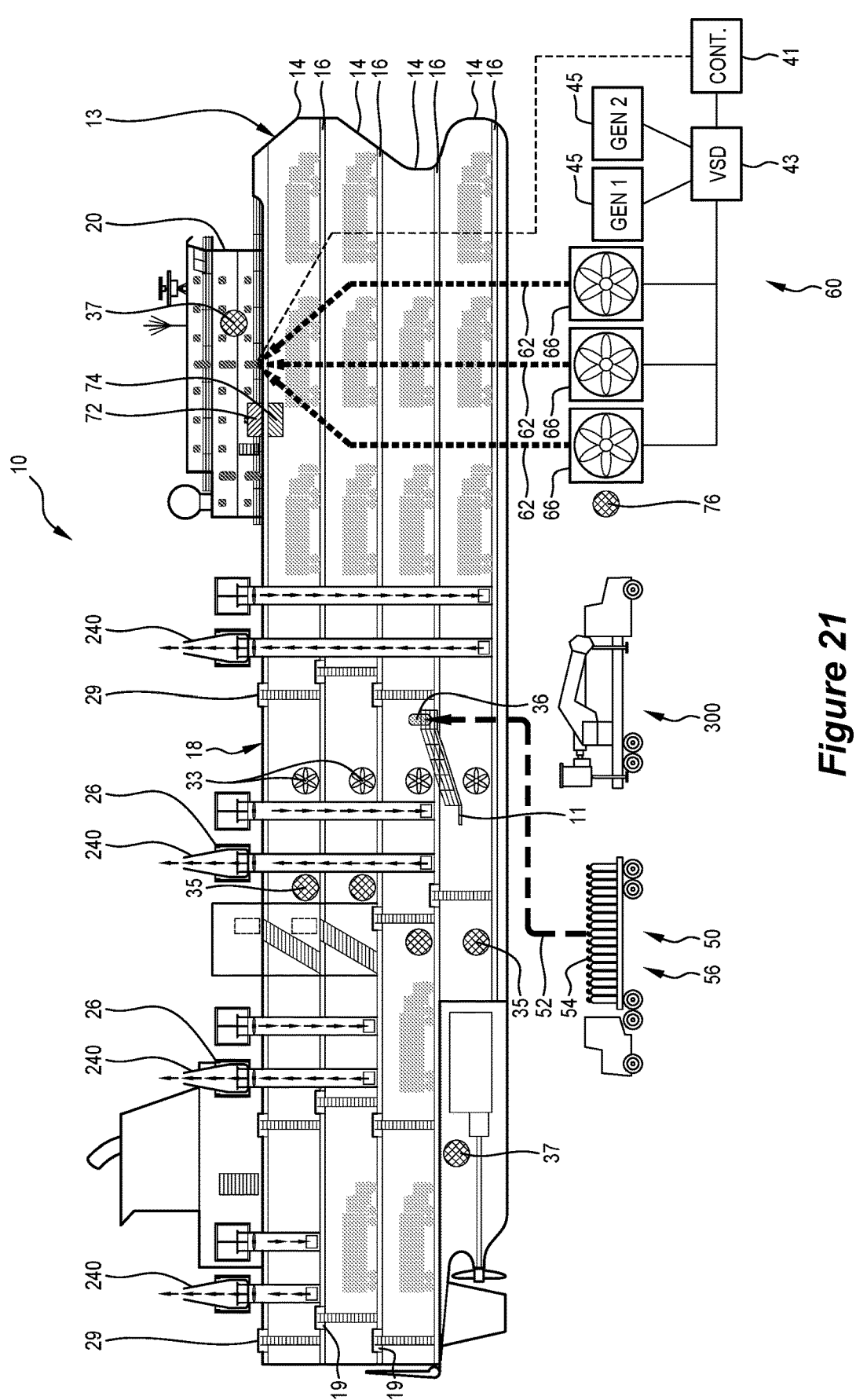
FIG. 21 is a side cross-sectional view of a RORO vessel that may be fumigated according to an alternative embodiment and shows a fumigant delivery system, an air pressure system, a temporary flexible exhaust according to an embodiment, and illustrates both a fumigation and ventilation operation.

The flexible temporary exhaust 58 described above may encounter a limitation wherein an air-tight seal cannot be formed at the stem or rising duct of the mechanical exhaust ventilator 26 due to pipework or other obstructions. FIG. 21 shows a RORO vessel 10 where the previously described flexible exhaust 58 is not able to be attached to the mechanical ventilator 26.

The fumigation operation of FIG. 21 is similar to that described above with an alternative flexible exhaust 240

(type II) attached within the exhaust mechanical ventilator 26. When ventilating the cargo zone 14 of fumigant, fresh air is drawn into the cargo zone 14 using supply mechanical ventilators 24 and/or pulled from the cargo zone 14 using the exhaust mechanical ventilators 26.

Figures 22, 23:
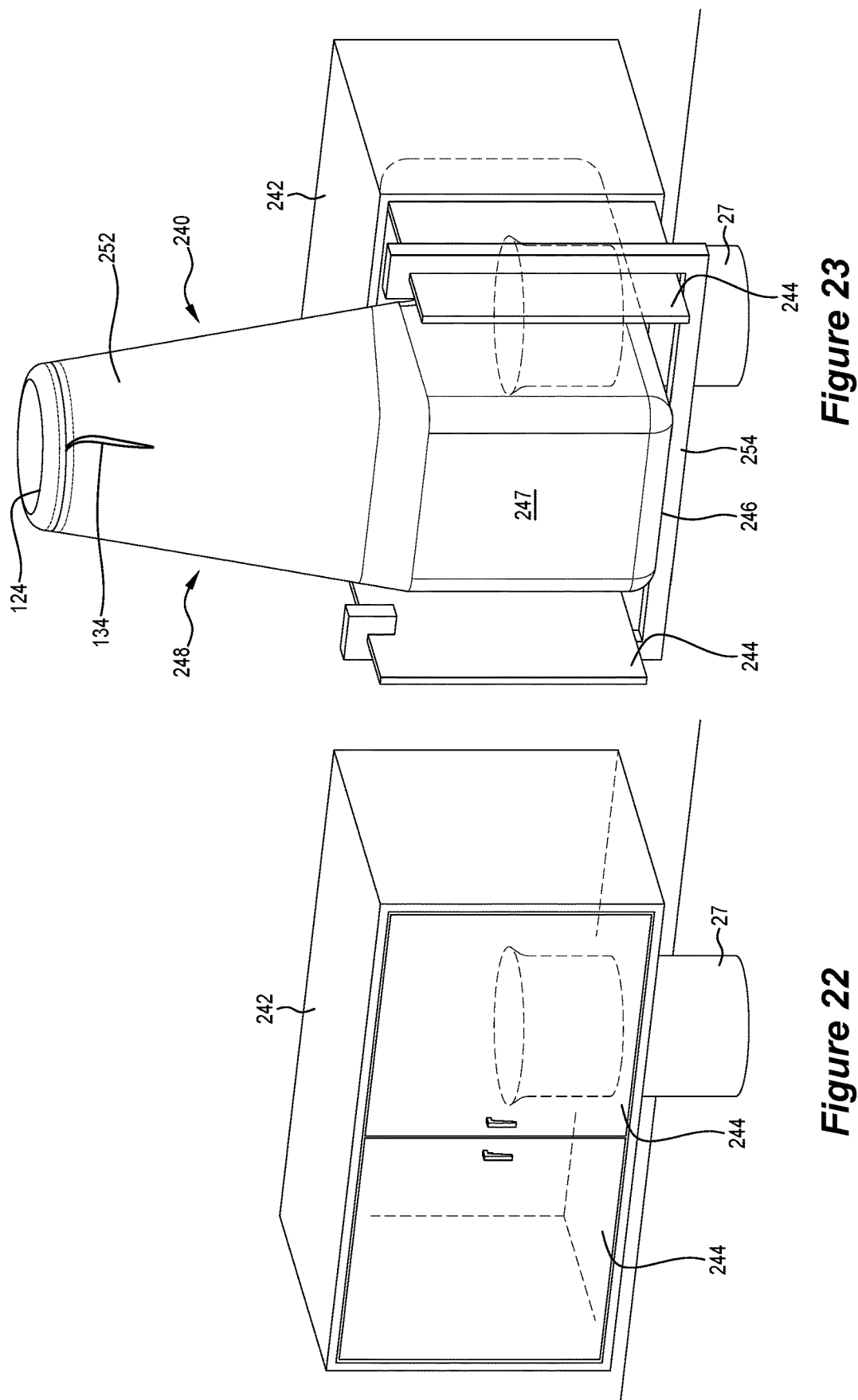
FIG. 22 is a mechanical exhaust ventilator with a housing as may be mounted on the weather deck of RORO vessel.
FIG. 23 is a flexible exhaust (type II) according to an embodiment installed on the mechanical ventilator of FIG. 22.

As can be seen in FIG. 22, the mechanical ventilators 26 on the weather deck 18 are typically housed within a ventilator housing 242 to protect the mechanical ventilator 26/exhaust fan 26a from the weather and other interference. The housing 242 has maintenance access doors 244 on one side that open to allow access to the top of the exhaust duct 27 and/or axial flow fan 26a (not shown). These doors are opened to install the alternative flexible exhaust 240.

Figures 24, 25:
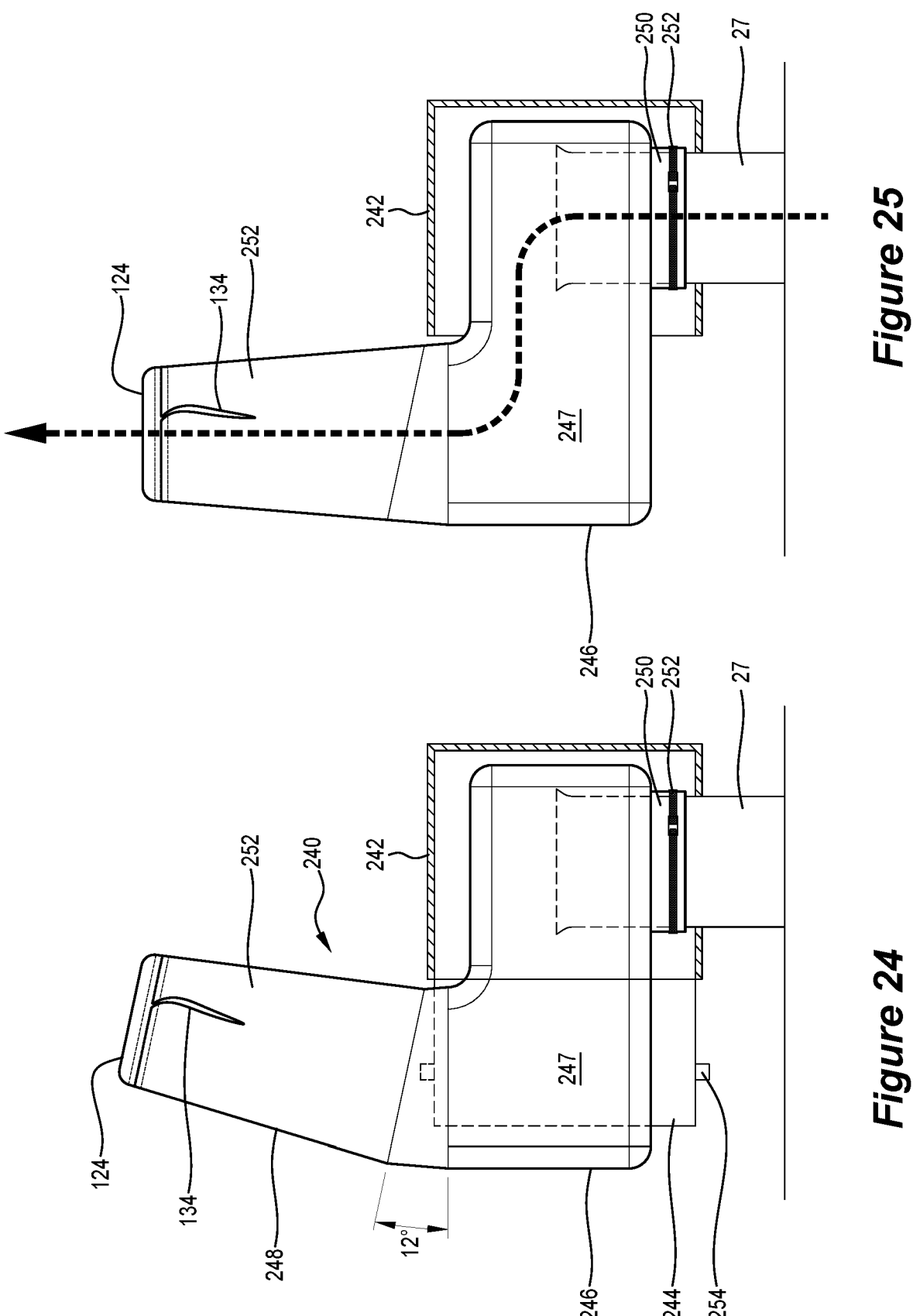
FIG. 24 is a side view of the flexible exhaust of FIG. 23.
FIG. 25 is a side view of the flexible exhaust of FIG. 23 during a ventilation operation.

FIGS. 23 to 25 show the alternative flexible exhaust 240 (type II) configured to attach to the top of the exhaust duct 27 and direct exhaust fumigant clear of the weather deck 18 during a ventilation operation. The alternative flexible exhaust 240 is made from gas-proof rip stop nylon and is of a substantially "L" shape to enable the flexible exhaust 140 to couple with the top of the exhaust duct 27 and to clear the housing 242. As is shown in FIG. 24 the alternative flexible exhaust 240 comprises a substantially horizontal portion 246 and a substantially vertical portion 248.

The substantially horizontal portion 246 is an inflatable plenum 247 which is a generally elongate cuboid but may be cylindrical. It has a circular connection 250 which is about 1 m in diameter, slightly larger than the axial flow fan 26a to accommodate and enclose the top of the exhaust duct 27 and which is secured using a tension/ratchet strap 252 creating a gas tight seal. The exhaust duct 27 affords a clean surface free of obstruction to which the plenum 247 may be attached. When inflated, the plenum extends out of the maintenance doors 244 and beyond the housing 242 so that the substantially vertical portion 248 is clear of the ventilator housing 242.

The substantially vertical portion 248 connects to the plenum 247 distal to the circular connection 250. The substantially vertical portion 248 tapers to a frustoconical velocity cone 252 with an upper downstream opening 124 and a drawstring 134 to vary the diameter of the upper downstream opening 124 to modify the velocity of the exhausted fumigant. The velocity cone 252 may be adjustable.

The velocity cone 252/substantially vertical portion 248 is inclined at an angle of about 12° to the horizontal, towards the ventilator housing 242 to allow for the force of the exhausted fumigant acting on the internal faces of the inflatable plenum 247 and/or the substantially vertical portion 248. As can be seen in FIG. 25, the velocity cone 252 is more vertical when exhausting fumigant due to the incline. The velocity cone 252/substantially vertical portion 248 extends vertically past the ventilator housing 242 to safely direct exhaust fumigant away from the weather deck 18 and the crew accommodation.

To further support the alternative flexible exhaust 240, a support assembly including at least one bracket 254 including cross members, as shown in FIG. 23, depends from the maintenance access doors 244 to retain the doors in the open position and to provide support to the bottom of the alternative flexible exhaust 240 during a venting operation. The support assembly may be adjustable to allow cross members to be set at a range of heights to support the plenum from underneath. An additional cross member may be fed through a loop on the chimney to hold the chimney towards the ventilator housing. Alternatively, another method of providing support to the inflatable structure would be to extend the lower part of the inflatable plenum to the deck of the vessel to support the inflatable structure from below.

Compensatory Over Pressure System

As is described above, the air pressure system 60 is operated throughout the fumigation operation and preferably throughout the ventilation operation, until all or substantially all of the gaseous fumigant has been removed from the cargo zones 14 and cargo 30. The gaseous fumigant is considered to have been removed or substantially removed from the cargo zones 14 and the cargo 30 when the sensors 35 of the high-range monitoring system detect a concentration of gaseous fumigant in the form of sulfuryl fluoride in concentrations equal to or less than 5 ppm.

As will be appreciated, during the ventilation operation, the pressure within the cargo area 13 may increase due to the supply of fresh air being provided by the supply mechanical ventilators 24. The air pressure system 60 accordingly operates to maintain the desired pressure differential between the cargo area 13 and the accommodation area 20 in light of any increase in pressure in the cargo area 13. It has been discovered that the air pressure system 60 is able to deliver air to the accommodation area 20 such that the accommodation area 20 is at a pressure of up to between 300 Pa and 1 kPa above mean sea level atmospheric pressure without significantly affecting the livability or usability the accommodation area 20 (whilst maintaining the desired pressure differential of at least 50 Pa above the pressure in the cargo area 13). However, the preferred maximum pressure in the accommodation area 20 is about 300 Pa above mean sea level atmospheric pressure.

If the pressure in the accommodation area 20 is close to or above 300 Pa above mean sea level atmospheric pressure, an alarm may be triggered to notify an operator to reduce the pressure in the cargo area 13. This may be achieved by adjusting the operation of the supply mechanical ventilators 24, and/or by opening one or more of the hatches 29 in the weather deck 18.

Alternative Ventilation Arrangements

The above described RORO vessel with supply, exhaust, and reverse mechanical ventilators is the most common arrangement, especially in the case of new RORO vessels. However, other arrangements can also be found in RORO vessels which present additional challenges for ventilation.

Passive Ventilation Through Vent Houses

In a first case, a RORO vessel may have no exhaust mechanical ventilators and instead rely on passive ventilation of the cargo zones by vent houses located upon the weather deck. Vent houses are commonly found on Pure Car and Truck Carrier type vessels (PCTC). Such a RORO vessel is illustrated in FIGS. 3 and 4.

Figure 3:
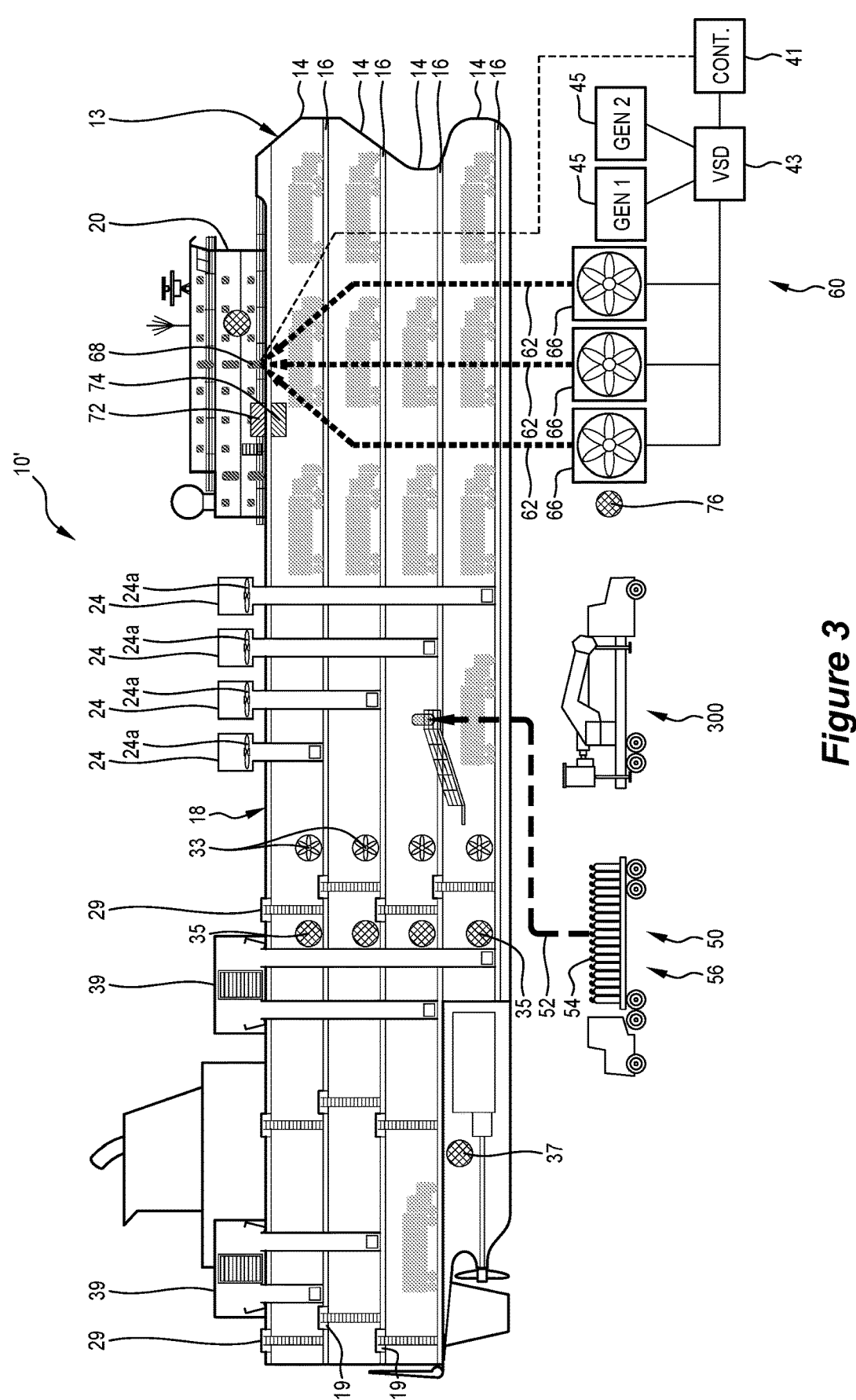
FIG. 3 is a side cross-sectional view of an alternative RORO vessel that may be fumigated according to an embodiment and shows a fumigant delivery system, an air pressure system, and a temporary flexible exhaust according to an embodiment, and illustrates a fumigation operation.
Figure 4:
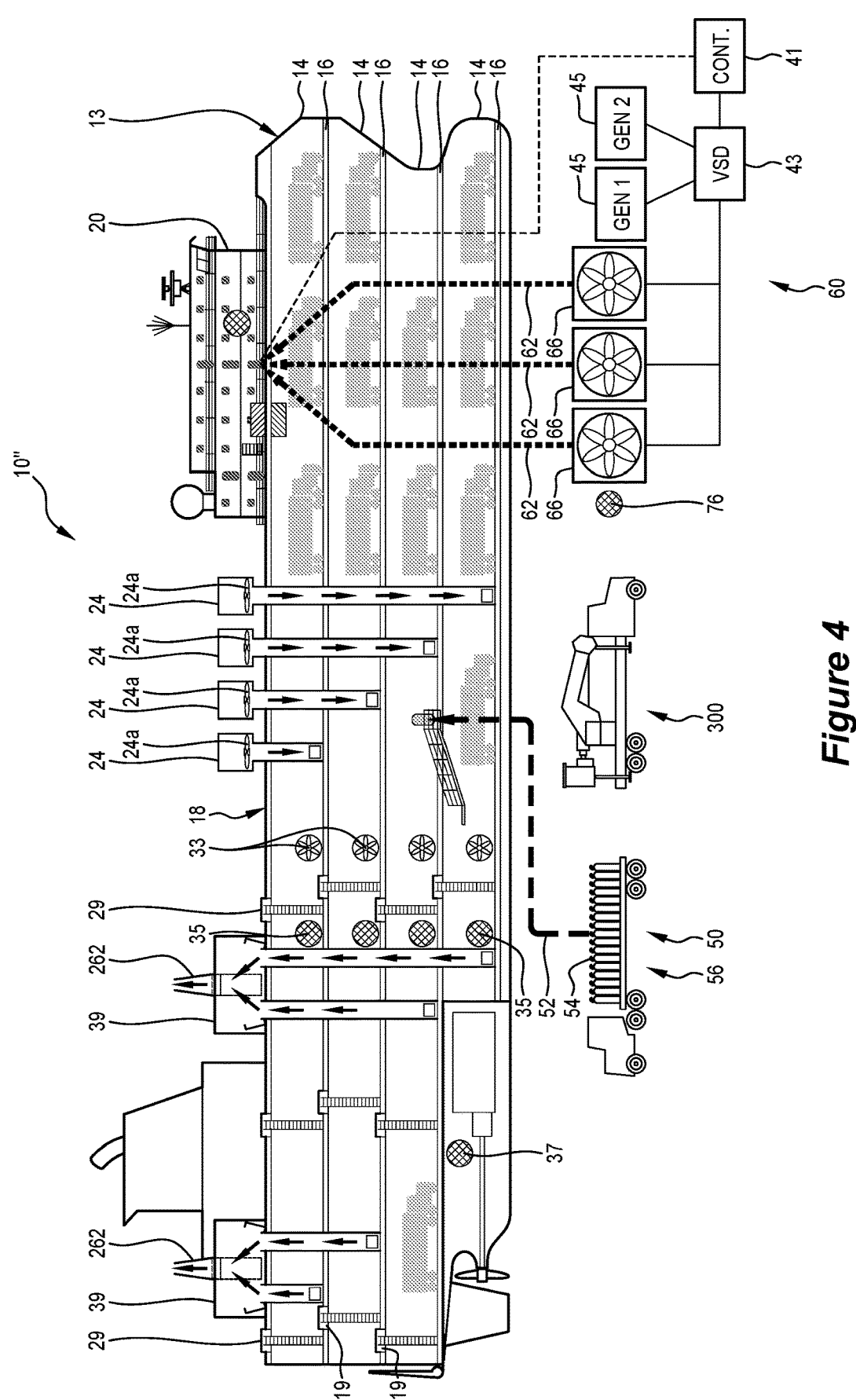
FIG. 4 is similar to FIG. 3, but illustrates a ventilation operation (which occurs after the fumigation operation)

As can be seen in FIG. 3, the vessel 10' includes supply mechanical ventilators 24 including associated fans 24*a* that draw air into each of the cargo zones 14, and a series of vent houses 39 located upon the weather deck 18. Each cargo zone 14 includes a dedicated vent house 39 and ductwork that enables passive ventilation of the respective cargo zone 14. The direction of the arrows in FIG. 4 show the direction of movement of air into the cargo zones 14 via the supply mechanical ventilators 24, and the direction of movement of air out of the cargo zones 14 via vent houses 39.

FIG. 3 illustrates the RORO vessel 10' when under fumigation. The fumigation system 50 and the air pressure system 60 illustrated in FIG. 3 are the same as that described herein in relation to FIGS. 1 and 2, and the fumigation operation is conducted substantially in the same manner as described herein in relation to the RORO vessel 10 illustrated in FIGS. 1 to 2. As is shown in FIG. 3, each of the vent houses 39 are provided with temporary flexible exhausts 262 (type Ill) as described in more detail below.

Alternatively, temporary flexible exhausts (not shown) of a type similar to temporary flexible exhausts 58 could be attached about the vent houses 39 in substantially the same manner as described above in relation to the exhaust mechanical ventilators 26 (see FIGS. 17 to 20 for example).

During the fumigation operation (shown in FIG. 3), the temporary flexible exhausts 58/262 may be tied at their downstream openings to prevent the escape of gaseous fumigant into the atmosphere above the weather deck 18.

FIG. 4 illustrates the ventilation operation. As can be seen in this figure, the downstream openings of the temporary flexible exhausts 58/262 are untied to enable air containing gaseous fumigant to be exhausted from the cargo zones 14 via the vent houses 39. During the ventilation operation, the supply mechanical ventilators 24 and their associated fans 24*a* are operated to draw fresh air into the cargo zones 14. The drawing of fresh air into the cargo zones 14 assists with the passive exhaust ventilation via the vent houses 39.

Type III Temporary Flexible Exhaust

Figure 26:
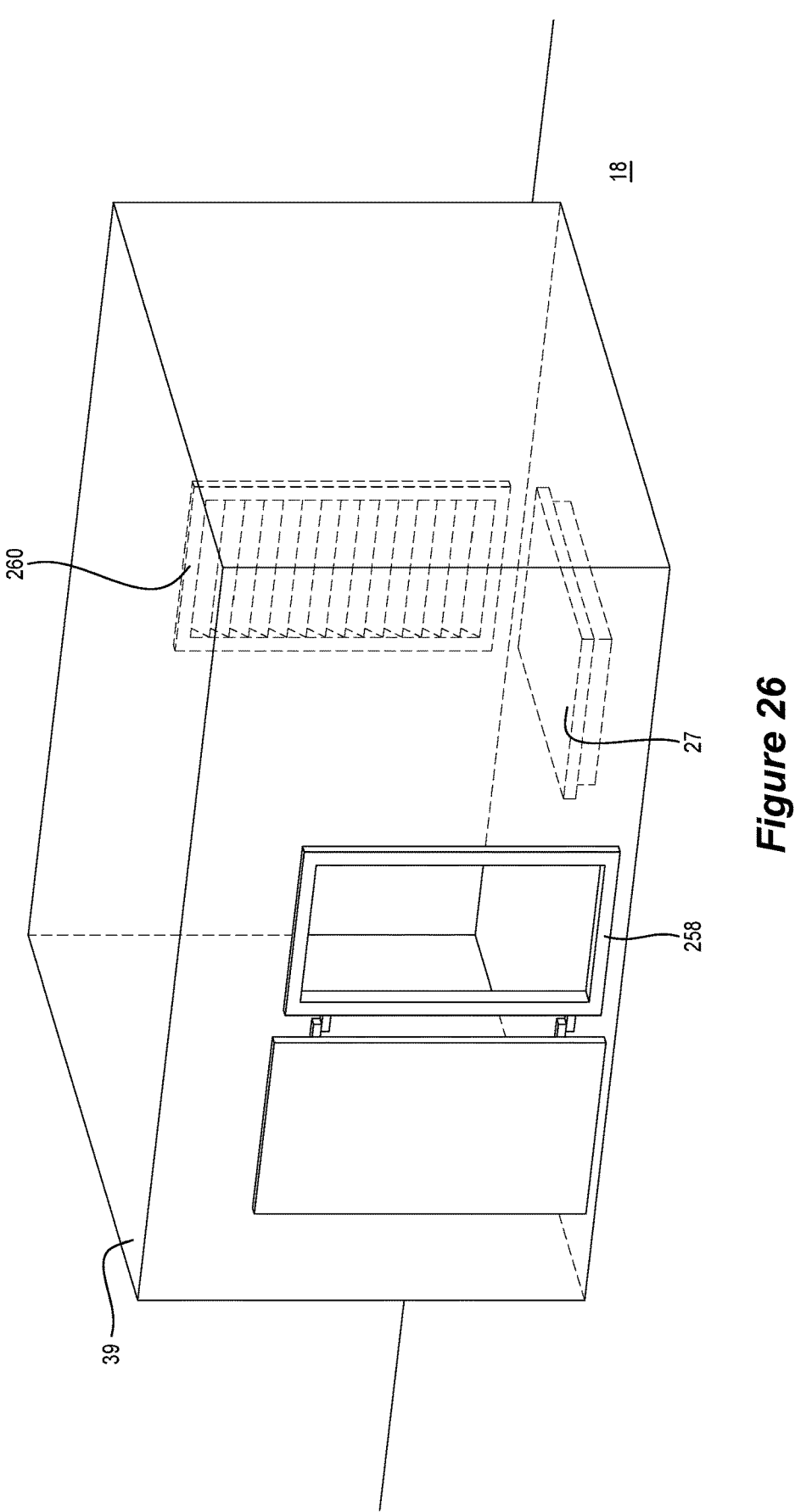
FIG. 26 is an exhaust vent house as may be mounted on the weather deck of a RORO vessel.
Figure 27:
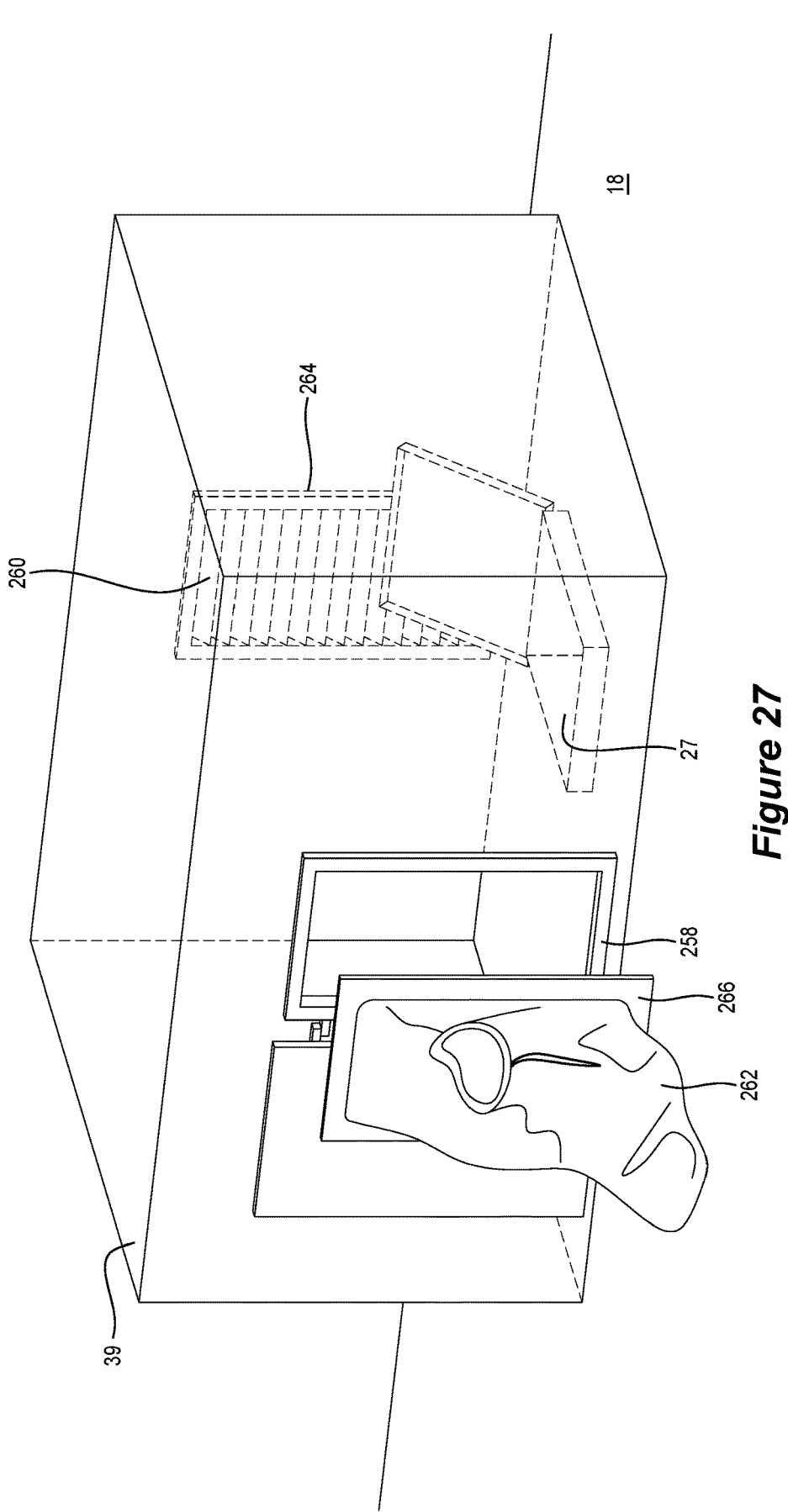
FIG. 27 is the vent house of FIG. 26 showing the installation location of a flexible exhaust according to an embodiment.
Figure 28:
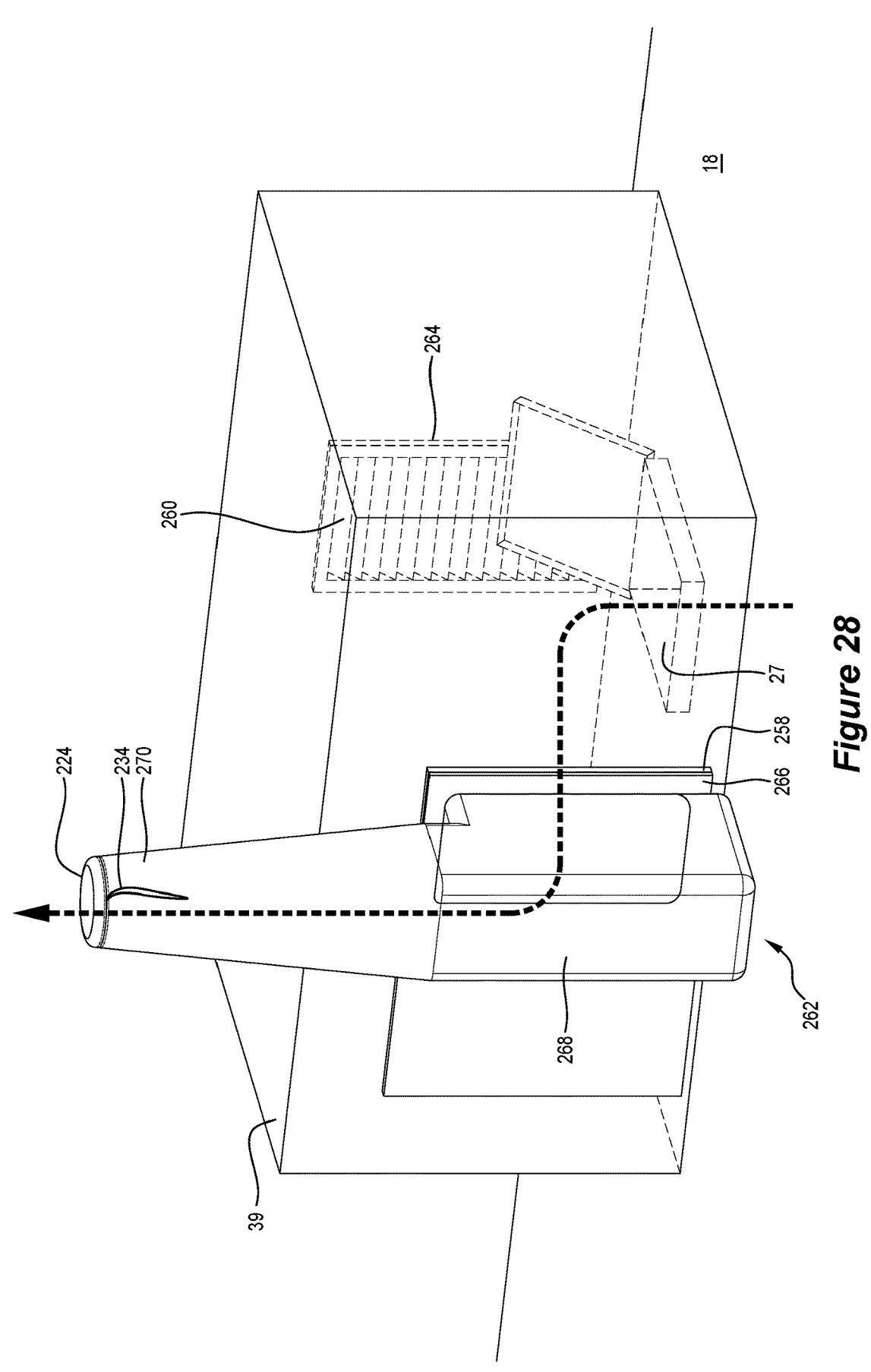
FIG. 28 is the vent house and flexible exhaust of FIG. 27 during a ventilation operation.

An alternative temporary flexible exhaust 262 is now presented in connection with FIGS. 26-28. Such a vessel is shown in FIG. 26, where the passive exhaust ducts 27 from the cargo zone 14 are housed inside a vent house 39, typically at the aft end 34 of the weather deck 18. The fumigation operation is the same as previously described. However the ventilation of the fumigant relies on the mechanical supply ventilators 24 to draw air into, and raise the pressure of, the cargo zone 14 being fumigated to expel the fumigant via the passive exhaust ducts 27.

FIG. 27 shows a typical vent house 39 installed on the weather deck 18 of the RORO vessel 10. The vent house 39 has an access doorway 258 that connects the inside of the vent house 39 to the weather deck 18 and which is typically closed unless maintenance or access is required. Louvered vents 260 in the walls of the vent house 39 are typically provided to expel the exhaust gases or fumigant from the inside of the vent house 39 to the atmosphere of the weather deck 18. The exhaust ducts 27 from the cargo zones 14 terminate on the floor inside the vent house 39.

Shown in FIG. 27 is a second alternative flexible exhaust 262 (type III) being installed on the access door 258 of a vent house 26. The louvered vent 260 in the wall of the vent house 39 is covered to prevent air flow by any conventional means such as a plastic sheet 264 secured with adhesive tape. In this arrangement, exhaust gas or fumigant is blocked from exiting the vent house 39 via the louvered vent 260 and is instead forced to vent via the access door 258. The second alternative flexible exhaust 262 is secured to the access doorway 258 so as to cover the doorway and direct air flow through the second alternative flexible exhaust 262, as shown in FIG. 29.

Referring to FIG. 28, the second alternative flexible exhaust 262 is inflated during a ventilation operation. The exhaust is made from gas-proof rip stop nylon. The connection point 266 of the second alternative exhaust 262 is an aluminium profile of a similar shape to that of the access doorway 258 (typically oval and generally one access doorway 258 per vent house) so that the connection point 266 can be secured to the access doorway 258 using clamps. Alternatively, the second alternative exhaust 262 may be attached to the access doorway 258 without the aluminium profile and instead with the use of adhesive tape.

The second alternative exhaust 262 comprises a plenum 268 that extends away from the access doorway 258 when inflated, a lower portion of the plenum 268 that extends downwards and towards the weather deck 18 to provide support to the second alternative exhaust 262, and an adjustable velocity cone 270 that extends upwards from the plenum 268 to direct exhaust fumigant away from the weather deck 18. The plenum may be an elongate cuboid or a generally cylindrical shape. The velocity cone 268 is frustoconical in shape with an upper downstream opening 224 at the uppermost point and a drawstring 234 to vary the diameter of the opening to modify the velocity of the exhausted fumigant.

To install the second alternative exhaust 262 to a vent house 39:

1. All supply ventilators are switched off;
2. The duct leading to the vent house is closed via its lid.
3. The maintenance door to the vent house is opened.
4. Plastic sheeting/corflute/other sheeting is fitted or taped over the ventilation louvres from the inside of the vent house.
5. The exhaust 262 is fitted to the access doorway 258.
6. The supply ventilators are turned on.
7. The vent house duct is opened to allow inflation of the second alternative exhaust 262.

Additionally, the exhaust 262 may be provided with ties to secure it to the vent house 256.

Ventilation Through Escape Trunks

In a second example, the preferred method is not possible due to incompatibility of the flexible exhausts described above due to the arrangement of the mechanical ventilators or vent houses or due to other circumstances.

In this case, ventilation could be achieved by use of the escape trunks. As is described above, the escape trunks may be in the form of hatches 29 (FIG. 1) that include ladders that extend downwardly into the uppermost cargo zone 14. Alternatively, the escape trunks may be in the form of staircases 31 (FIG. 5) that lead into the uppermost cargo zone 14. With the use of an intake fan, such as an axial or mixed flow fan in the escape trunk, a temporary exhaust 58 may be used. However, such a temporary exhaust does not need to fit over a structure such as a mechanical ventilator. Thus, the temporary exhaust need not be flexible. Additionally, the temporary exhaust need not be shaped as a velocity cone and cylindrical conduits or other straight tubes could be employed.

As will be appreciated by the person skilled in the art, this alternative method of ventilation could also be used with the RORO vessel 10 illustrated in FIG. 1 and the RORO vessel 10' illustrated in FIG. 3.

Referring initially to FIG. 5, it can be seen that the RORO vessel 10" includes, by way of example, supply mechanical ventilators 24 and exhaust mechanical ventilators 26. It will be appreciated that the RORO vessel of FIG. 5 need not have supply mechanical ventilators 24 or exhaust mechanical ventilators 26 for the method of the second case to be employed. The RORO vessel 10" also includes escape trunks in the form of ladders and hatches 29, and escape trunks in the form of staircases 31.

FIG. 5 illustrates the RORO vessel 10" when under fumigation. The fumigation operation is conducted substantially in the same manner as described above. As can be seen in FIG. 5, prior to commencing the fumigation operation, temporary flexible exhausts 58 are attached to respective hatches 29 and staircases 31 and are tied at their downstream openings. Although only a single hatch 29 and a single staircase 31 are shown with attached temporary flexible exhausts 58 in FIG. 5, it will be appreciated that a plurality of the hatches 29 and staircases 31 will be fitted with temporary flexible exhausts 58. FIG. 5 also illustrates two hatches 29 that include temporary bulkheads 154 within axial or mixed flow fans 164 and respective flexible ducts 159 leading into the uppermost cargo zone 14. As is described below, during the ventilation operation, the hatches 29 including the axial or mixed flow fans 164 are operated as supply ventilators in order to draw fresh air into the cargo area 13. During the fumigation operation however, the hatches 29 including the temporary bulkheads 154 and axial or mixed flow fans 164 are covered by removable covers 188 in order to prevent the escape of air containing gaseous fumigant into the atmosphere above the weather deck 18. Although FIG. 5 only illustrates hatches 29 that include axial or mixed flow fans 164 for use as supply ventilators during the ventilation operation, it will be appreciated that staircases 31 including axial or mixed flow fans 164 could also be used as supply ventilators.

In an arrangement, approximately half of the total number of escape trunks (either hatches 29 or staircases 31) are fitted with flexible temporary exhausts 58, and the remaining half of the total number of escape trunks (either hatches 29 or staircases 31) are fitted with respective temporary bulkheads and axial or mixed flow fans 164 for use as supply ventilators during the ventilation operation.

Figure 6:
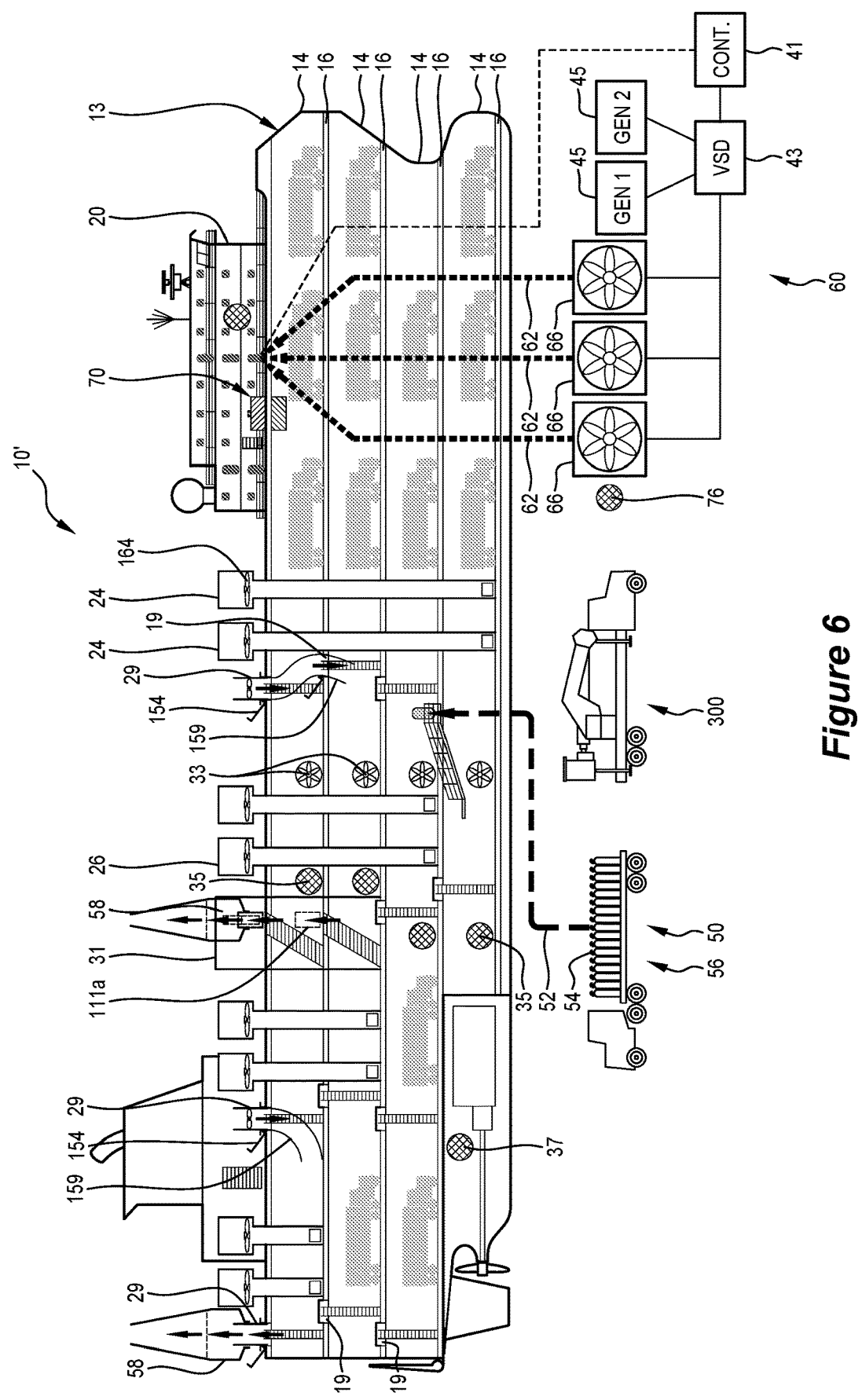
FIG. 6 is similar to FIG. 5 but shows a ventilation operation (which occurs after the fumigation operation)

FIG. 6 illustrates the ventilation operation. Specifically, firstly, the downstream openings of the flexible temporary exhausts 58 are untied and the covers 188 covering the hatches 29 are removed. The uppermost cargo zone 14 is ventilated prior to ventilating the other cargo zones 14. As is described above, the hatches 29 including the axial or mixed flow fans 164 are operated as supply ventilators to supply fresh air into the uppermost cargo zone 14. As illustrated in FIG. 6, the left-most hatch 29 including the axial or mixed flow fan 164 also includes a flexible duct 159. The flexible duct 159 includes an downstream opening located in the uppermost cargo zone 14, which thereby supplies fresh air into the uppermost cargo zone 14. The supply of fresh air into the uppermost cargo zone 14 causes air in the uppermost cargo zone 14 to be exhausted via the hatches 29 and staircases 31 that are fitted with flexible temporary exhausts 58.

Once the concentration of gaseous fumigant in the uppermost cargo zone 14 is at or below 5 ppm (for gaseous fumigant comprising sulfuryl fluoride), the specially trained fumigation personnel enter the uppermost cargo zone via the hatches 29 or staircases 31. The specially trained fumigation personnel then open the hatches 19 that lead into the second uppermost cargo zone 14 from the uppermost cargo zone 14. The specially trained fumigation personnel then route the flexible ducts 159 of the supply hatches 29 into the second uppermost cargo zone 14 such that the downstream openings of the flexible ducts 159 are located in the second uppermost cargo zone 14. In this manner, fresh air may be supplied into the second uppermost cargo zone 14. It will be appreciated that FIG. 6 only shows that the right-most hatch 29 including the axial or mixed flow fan 164 includes the flexible duct 159 with its downstream opening located on the second uppermost cargo zone 14.

After the flexible ducts 159 have been routed to the second uppermost cargo zone 14, the specially trained fumigation personnel then exit the cargo area 13. Once clear of the cargo area 13, the ventilation operation is recommenced and the second uppermost cargo zone 14 is ventilated. Specifically, fresh air is drawn into the second uppermost cargo zone 14 via the opened hatches 19 and the hatches 29 that include the axial or mixed flow fans 164. The supply of fresh air to the second uppermost cargo zone 14 causes air containing gaseous fumigant to be exhausted from the second uppermost cargo zone 14 via the opened hatches 19 and the hatches 29 and staircases 31 that include the flexible temporary exhausts. Once the concentration of gaseous fumigant in the second uppermost cargo zone 14 is at or below 5 ppm (for gaseous fumigant comprising sulfuryl fluoride), the specially trained fumigation personnel enter the second uppermost cargo zone via the hatches 29 or staircases 31 and the internal hatches 19.

Then, the specially trained fumigation personnel open the hatches 19 to the second lowermost cargo zone 14 and route the flexible ducts 159 such that their downstream openings are located in the second lowermost cargo zone 14. The specially trained fumigation personnel then exit the cargo area 13. Once clear of the cargo area 13, the ventilation operation is recommenced and the second lowermost cargo zone 14 is ventilated. This process is repeated until all of the cargo zones 14 have been ventilated.

Thus, as is described above, in this alternative method of ventilation, the cargo area 13 is ventilated by fresh air positively drawn through the hatches 29 and/or staircases 31 by axial or mixed flow fans 164. In essence, the hatches 29 and/or staircases 31 that include the axial or mixed flow fans 164 act as supply ventilators and perform a similar function to the mechanical supply ventilators 24.

Any of the foregoing arrangements which result in passive exhaust of air from the cargo zones are less desirable in view of the potential pressure buildup in the cargo zones which could conceivably exceed the positive pressure applied to the accommodation and other crew areas.

As will be appreciated by a person skilled in the art, a combination of methods described above could be used to achieve the fumigation of a RORO vessel 10. For example combining the alternative methods to draw fresh air into the cargo area 13 via mechanical supply ducts 25 during ventilation and to exhaust fumigant via hatches 29 or stairs 31 in the escape trunk is also possible.

Assessment as to an appropriate arrangement may include an inspection of the ship. For example, a ship which is in poor condition due to fatigue resulting in hairline cracks in metal sheeting between various compartments would be unsuited to such an arrangement. However, if the ship is in good condition such an arrangement may suffice.

Insect Net

As is shown in FIG. 18, the flexible exhaust 58 includes an insect net 132 located within the inflatable conduit 120 which is configured to capture and prevent any live insects from being exhausted into the atmosphere during the ventilation operation. The insect net 132 is located generally above the exhaust mechanical ventilator 26 generally closer to the upstream lower opening 122 than the downstream upper opening 124. The insect net 132 may be disposed approximately 30 cm above the mechanical ventilator. This keeps the centre of mass lower which provides better aerodynamics for flexible exhaust 58. The insect net 132 has an approximate grid side in a range of 0.5 mm to 10 mm. The insect net 132 can be removable i.e. velcroed in place, however it is ideally sewn/fixed in place.

Alternate safeguard methods include: a) first covering the exhaust mechanical ventilator with an insect net and fastening at the base of the exhaust mechanical ventilator, and then covering the net-covered exhaust mechanical ventilator with a flexible exhaust 58; or b) fixing an insect net over the intake (exhaust duct) in the cargo zone, to prevent insects from being sucked into the exhaust duct and from being exhausted into the atmosphere (in this example, no insect net is present in the flexible exhaust 58).

Type II and type III flexible exhausts 240, 262 may also be fitted with insect nets as per above.

Adjustable Upper Opening

The use of a velocity cone is intended to narrow the shape of the conduit 58 from the first opening which is intended to be large and fit over the structure of the exhaust mechanical ventilator 26 to the upper second opening which is intended to be of a size which keeps the flexible conduit 58 in an inflated configuration. Additionally, the outflow from an exhaust mechanical ventilator 26 is downward and the flexible conduit 58 needs to be shaped to create a plenum chamber below the exhaust mechanical ventilator 26. Additionally, adequate clearance around the exhaust mechanical ventilator 26 is required for the upward passage of exhausted air. These factors determine a large base for the flexible conduit 58, thereby requiring a frustoconical tapering to a smaller second upper opening 124.

As is shown in FIGS. 17 to 20, the flexible exhaust 58 further includes a drawstring 134 disposed about the upper opening 124 to thereby adjust the cross-sectional area of the upper opening 124. The adjustment of the downstream upper opening 124 may be achieved by initially drawing in the opening 124 via the drawstring 134 and allowing the pressure of the exhausted air to automatically adjust the opening 124. FIG. 18 illustrates the adjustability in the cross-sectional area of the upper opening 124 by use of the drawstring 134. As is shown in this figure, the opening 124 is adjustable between a first relatively unrestricted open configuration in which the upper portion 130 of the flexible exhaust 58 is generally cylindrical in overall form, and a second relatively restricted configuration in which the upper portion 130 is generally frustoconical in overall form. Typically, the opening 124 is initially arranged in the second relatively restricted configuration, with the force of the ventilated air enabling the opening 124 to adjust itself to an appropriately open configuration. Typically, the cross-sectional area of the open configuration may correspond to the cross-sectional area of the output fan. The adjustable opening allows self-adjustment of the exhaust 58 to create an appropriately dimensioned velocity cone commensurate with the output of the ventilated air.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A control system for a roll-on/roll-off (RORO) vessel, the control system comprising a controller configured to:
   receive at least one pressure reading or at least one differential pressure reading from at least one of a selected area of the vessel or a cargo area during a fumigation;
   in response to the at least one reading, control an air delivery to the selected area of the vessel in order to maintain a selected minimum pressure differential between the selected area and the cargo area with a pressure of the selected area being greater than a pressure of the cargo area; and
   maintain the selected minimum pressure differential throughout the fumigation and a subsequent exhaust of a fumigant from the cargo area.

2. The control system as claimed in claim 1, wherein the selected minimum pressure differential is at least about 50 Pa, or between about 50 Pa and about 100 Pa.

3. The control system as claimed in claim 1, wherein the selected minimum pressure differential is pre-selected.

4. The control system as claimed in claim 1, wherein the control system is responsive to at least one of (i) one or more pressure sensors or (ii) differential pressure sensors, and is further configured to control one or more air supply fans to supply air to the selected area to maintain the selected minimum pressure differential.

5. The control system as claimed in claim 4, wherein the control system is configured to control at least a speed of the one or more fans via a variable speed drive.

6. The control system as claimed in claim 1, wherein the control system is configured to perform low range monitoring to detect at least one of (i) gaseous fumigant, (ii) carbon dioxide, (iii) carbon monoxide, or (iv) other volatile organic compounds (VOCs) at least one of (a) within the selected area or (b) at an air intake for a delivered air.

7. A method of pre-configuring a control system which is ancillary to a roll-on/roll-off (RORO) vessel, the method comprising pre-configuring a controller of the ancillary control system such that the controller is configured to:

receive at least one pressure reading or at least one differential pressure reading from at least one of a selected area of the vessel or a cargo area during a fumigation;

in response to the at least one reading, control an air delivery to the selected area of the vessel in order to maintain a selected minimum pressure differential between the selected area and the cargo area with a pressure of the selected area being greater than a pressure of the cargo area; and maintain the selected minimum pressure differential throughout the fumigation and a subsequent exhaust of a fumigant from the cargo area.

8. The method as claimed in claim 7, further comprising preconfiguring the control system to maintain the selected minimum pressure differential of at least one of (i) at least about 50 Pa, or (ii) between about 50 Pa and about 100 Pa.

9. The method as claimed in claim 8, further comprising preconfiguring the control system to maintain or pre-select at least the selected minimum pressure differential.

10. The method as claimed in claim 7 further comprising preconfiguring the ancillary control system to control one or more air supply fans to deliver the air to the selected area.

11. The method as claimed in claim 7, further comprising pre-configuring the control system or an additional ancillary control system to perform low-range monitoring to detect at least one of (i) gaseous fumigant, (ii) carbon dioxide, (iii) carbon monoxide, or (iv) other volatile organic compounds (VOCs) at least one of (a) within the selected area or (ii) at an air intake for the delivered air, wherein the controller is configured to control air delivery in response to an output of the low range monitoring.

12. A system for fumigating a vessel wherein the system is ancillary to the vessel, the system comprising:

a fumigant delivery system configured to deliver a fumigant to a cargo area of the vessel; and an air pressure system configured to maintain a selected minimum pressure differential between a selected area of the vessel above the cargo area and the cargo area, such that a pressure of the selected area is greater than a pressure of the cargo area.

13. The system as claimed in claim 12, wherein the vessel is a roll-on/roll-off vessel.

14. The system as claimed in claim 12, wherein the air pressure system comprises a controller configured to maintain the selected minimum pressure differential throughout a fumigation and an exhaust of the fumigant.

15. The system as claimed in claim 12, wherein an air intake for the air pressure system is remote from the one or more fumigant delivery sites and one or more exhaust sites.

16. The system as claimed in claim 15, wherein the air intake is more than about 30 metres from the one or more fumigant delivery sites and the one or more exhaust sites for an exhausted fumigant.

17. The system as claimed in claim 15, wherein the air intake is located quayside of the vessel, outwardly of a hull of the vessel, or at a forward end of the vessel.

* * * * *